(12) United States Patent
Biolchini, Jr.

(10) Patent No.: US 10,327,792 B2
(45) Date of Patent: Jun. 25, 2019

(54) AMBIDEXTROUS LOCKING CLAMP SYSTEM

(71) Applicant: Robert F. Biolchini, Jr., Jackson, WY (US)

(72) Inventor: Robert F. Biolchini, Jr., Jackson, WY (US)

( * ) Notice: Subject to any disclaimer, the term of this patent is extended or adjusted under 35 U.S.C. 154(b) by 132 days.

(21) Appl. No.: 15/070,272

(22) Filed: Mar. 15, 2016

(65) Prior Publication Data

US 2016/0192958 A1 Jul. 7, 2016

Related U.S. Application Data

(63) Continuation-in-part of application No. 13/272,676, filed on Oct. 13, 2011, now Pat. No. 9,427,245, which is a continuation-in-part of application No. 11/733,280, filed on Apr. 10, 2007, now Pat. No. 8,070,771, which is a continuation-in-part of application No. 10/909,623, filed on Aug. 2, 2004, now Pat. No. 7,758,609, said application No. 13/272,676 is a continuation-in-part of application No. 10/909,623, filed on Aug. 2, 2004, now Pat. No. 7,758,609.

(51) Int. Cl.
*A61B 17/28* (2006.01)
*A61B 17/122* (2006.01)
*A61B 17/00* (2006.01)

(52) U.S. Cl.
CPC ........ *A61B 17/2833* (2013.01); *A61B 17/122* (2013.01); *A61B 2017/0042* (2013.01); *A61B 2017/2808* (2013.01); *A61B 2017/2837* (2013.01)

(58) Field of Classification Search
CPC ......... A61B 17/1114; A61B 2017/1139; A61B 2017/1117; A61B 17/12163; A61B 2017/00876
See application file for complete search history.

(56) References Cited

U.S. PATENT DOCUMENTS

| 3,157,075 | A |   | 11/1964 | Filia |
|---|---|---|---|---|
| 3,417,752 | A |   | 12/1968 | Butler |
| 3,873,016 | A | * | 3/1975 | Fishbein ............ A61B 17/0684 227/121 |

(Continued)

*Primary Examiner* — Richard G Louis
(74) *Attorney, Agent, or Firm* — David Guerra

(57) ABSTRACT

An ambidextrous locking clamp system for providing a user the ability to use the right or left hand to engage and disengage a ratcheting means on the clamp. The clamp has hingedly connected first and second elongated members each with a finger engaging member arm, a finger engaging member, a working head, and a latching member featuring ratcheting teeth. The teeth face each other in a direction parallel with a longitudinal axis of the clamp. The teeth are engaged by moving the finger engaging members toward each other in an engaging motion, and are disengaged by sliding them in a disengaging motion perpendicular to the engaging motion with opposing force applied to the finger engaging members. A space is defined between the finger engaging member arms and the finger engaging members. The latching members extend into the space from where the finger engaging members transition from their corresponding finger engaging member arms.

20 Claims, 27 Drawing Sheets

(56) References Cited

U.S. PATENT DOCUMENTS

| | | |
|---|---|---|
| 3,913,586 A | 10/1975 | Baumgarten |
| 3,978,584 A | 9/1976 | Mayer |
| 4,452,246 A | 6/1984 | Bader et al. |
| 4,823,792 A | 4/1989 | Dulebohn et al. |
| 5,176,702 A | 1/1993 | Bales |
| 5,626,608 A | 5/1997 | Cuny |
| 6,187,003 B1 * | 2/2001 | Buysse .............. A61B 17/2816 30/342 |
| 6,223,440 B1 | 5/2001 | Rashman |
| 6,397,478 B1 | 6/2002 | Bornancini |
| 2004/0106947 A1 | 6/2004 | Propp |

* cited by examiner

AMBIDEXTROUS LOCKING CLAMP SYSTEM

CROSS REFERENCE TO RELATED APPLICATION

This application is a continuation-in-part under 35 U.S.C. § 120 based upon co-pending U.S. patent application Ser. No. 13/272,676 filed Oct. 13, 2011, which is incorporated herein by reference in its entirety.

BACKGROUND OF THE INVENTION

Field of the Invention

The present invention relates to an ambidextrous locking clamp system for use in connection with clamping instruments, such as surgical clamps, forceps, or hemostats. The ambidextrous locking clamp system has particular utility in connection with manipulating a hand tool to engage latching members by moving flexible members toward each other which, and to disengage the latching members by sliding the latching members in a motion perpendicular to the engaging motion thereby flexing the flexible members away from each other when an opposing force is applied to the flexible members. The opposing force is produced by pushing with a thumb of an operating hand of a user on one of the flexible members and pulling with fingers of the operating hand on the other flexible member thereby slidably separating the latching members.

Description of the Prior Art

Ambidextrous locking clamps, forceps or hemostats are desirable for allowing a right or left-handed user to use a single hand operated clamp, forceps or hemostat device. These hand operated devices have been manufactured in the past for either a right hand or left hand user. This manufacturing process has some disadvantages in that the manufacturer would have to make a decision as to how many right handed and left handed devices to fabricate. In most cases the decision is made to manufacture more right-handed devices than left handed devices. Therefore, it is well known that it is very difficult for a left-handed user to operate a right-handed device.

Hand operated locking clamps, forceps and hemostats are known in the art. These devices include a pair of elongated members joined by a hinge. The hinge is usually a hinge pin extending through both elongated members. One end of the elongated members features a working head, usually a griping jaw or cutting edges. The other end of the elongated members feature a finger engaging loop, with a set of ratchet teeth extending out therefrom towards the ratchet teeth of the finger loop of the second elongated member. The ratchet teeth are orientated so that they engage each other when the finger loop ends are brought together. These devices are mainly used in the medical industry for a wide variety of uses, but they are also used in the fly fishing, model building, and electrical industries.

During operation of a standard right handed hand operated device, the user inserts his or her thumb into one loop, the middle finger in the opposite loop, and the index finger would rest on the top of the middle finger loop for support and control of the device. To engage the working head the user squeezes the thumb and middle finger together guided by the index finger. The device is locked in the close position by further squeezing the loops together until the ratchet teeth members engage each other. To release, the thumb pushes away from the palm of the hand and the middle finger pulls toward the palm of the hand. This motion makes the ratchet teeth members flex away from each other and disengage.

The difficulty lies when a left-handed user tries to operate a right-handed device. It is difficult for a left-handed user to pull with the thumb and push with the middle finger. This is not a natural hand motion.

While the above-described devices fulfill their respective, particular objectives and requirements, the aforementioned patents do not describe an ambidextrous hand operated device that allows the use of the device by a right or left handed user through the engaging of latching members by moving flexible members toward each other which, and the disengaging of the latching members by sliding the latching members in a motion perpendicular to the engaging motion thereby flexing the flexible members away from each other when an opposing force is applied to the flexible members. Wherein, the opposing force is produced by pushing with a thumb of an operating hand of a user on one of the flexible members and pulling with fingers of the operating hand on the other flexible member thereby slidably separating the latching members.

Therefore, a need exists for a new and improved ambidextrous locking clamp system that can be used for manipulating objects with a tool having removable and interchangeable components. In this regard, the present invention substantially fulfills this need. In this respect, the ambidextrous locking clamp system according to the present invention substantially departs from the conventional concepts and designs of the prior art, and in doing so provides an apparatus primarily developed for the purpose of manipulating a hand tool to engage latching members by moving flexible members toward each other which, and to disengage the latching members by sliding the latching members in a motion perpendicular to the engaging motion thereby flexing the flexible members away from each other when an opposing force is applied to the flexible members. The opposing force is produced by pushing with a thumb of an operating hand of a user on one of the flexible members and pulling with fingers of the operating hand on the other flexible member thereby slidably separating the latching members.

SUMMARY OF THE INVENTION

In view of the foregoing disadvantages inherent in the known types of hand operated locking devices now present in the prior art, the present invention provides an improved ambidextrous locking clamp system, and overcomes the above-mentioned disadvantages and drawbacks of the prior art. As such, the general purpose of the present invention, which will be described subsequently in greater detail, is to provide a new and improved ambidextrous locking clamp system and method which has all the advantages of the prior art mentioned heretofore and many novel features that result in a ambidextrous locking clamp system which is not anticipated, rendered obvious, suggested, or even implied by the prior art, either alone or in any combination thereof.

To attain this, the present invention essentially comprises an ambidextrous locking clamp for providing a user the ability to alter the configuration of a hand operated device allowing a right hand or left hand user to operate the device. The ambidextrous locking clamp has a first and second elongated members hingedly connected. The elongated members each have a finger engaging member arm, a finger engaging member, a working head, and a latching member featuring ratcheting teeth. The ratcheting teeth face each other in a direction parallel with a longitudinal axis of the clamp, and are releasably engageable with each other when the finger engaging members are moved toward each other. A first and second member space is defined between the first and second finger engaging member arms and the first and second finger engaging members. The latching members extend into the space from where the finger engaging members transition from their corresponding finger engaging member arms.

The ratcheting teeth are engaged by moving the finger engaging members toward each other in an engaging motion. The ratcheting teeth are disengaged with each other by sliding the ratcheting teeth apart by a disengaging motion perpendicular to the engaging motion resulting in moving the latching members away from each other when an opposing force is applied to the finger engaging members. The perpendicular motion can be produced in either direction so as to accommodate a right-handed or left-handed user.

Additionally, the present invention may comprise the first and second latching members each featuring a first arm section, and a second arm section extending from the first arm section, respectively. The first arm section of the first latching member extends from a first member transitioning area and is received in the first member space. The first arm section of the second latching member extends from second member transitioning area and is received in the second member space.

There has thus been outlined, rather broadly, the more important features of the invention in order that the detailed description thereof that follows may be better understood and in order that the present contribution to the art may be better appreciated.

The invention may also include a variety of latching members, such as, but not limited to, rigid latching members, flexible latching members, flexible armed latching members, and ratcheting heads. There are, of course, additional features of the invention that will be described hereinafter and which will form the subject matter of the claims attached.

Numerous embodiments, features and advantages of the present invention will be readily apparent to those of ordinary skill in the art upon a reading of the following detailed description of presently preferred, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an embodiment of the present invention to provide a new and improved ambidextrous locking clamp system that has all of the advantages of the prior art locking clamps and none of the disadvantages.

It is another embodiment of the present invention to provide a new and improved ambidextrous locking clamp system that may be easily and efficiently manufactured and marketed.

An even further embodiment of the present invention is to provide a new and improved ambidextrous locking clamp system that has a low cost of manufacturing with regard to both materials and labor, and which accordingly is then susceptible of low prices of sale to the consuming public, thereby making such ambidextrous locking clamp system economically available to the buying public.

Still another embodiment of the present invention is to provide a new ambidextrous locking clamp system that provides in the apparatuses and methods of the prior art some of the advantages thereof, while simultaneously overcoming some of the disadvantages normally associated therewith.

Lastly, it is an object of the present invention to provide a new and improved method of using the ambidextrous locking clamp system by engaging the first and second member ratcheting teeth with each other by an engaging motion provided by the operating hand of a user until the ratcheting teeth overlap one another in succession to a user desired tension. The engaging motion is produced by moving the first and second finger engaging members toward each other. The ratcheting teeth are disengaged by a disengaging motion perpendicular to the engaging motion resulting in moving the first and second latching members away from each other when an opposing force. The disengaging motion is produced by move the first and second members in opposite directions when an opposing force is applied to the first and second finger engaging members by pushing with a thumb of the operating hand of the user on at least one of the first and second finger engaging members and pulling with at least one finger of the operating hand on the other of the first and second finger engaging members thereby slidably separating the ratcheting teeth out of engagement.

These together with other embodiments of the invention, along with the various features of novelty that characterize the invention, are pointed out with particularity in the claims annexed to and forming a part of this disclosure. For a better understanding of the invention, its operating advantages and the specific embodiments attained by its uses, reference should be had to the accompanying drawings and descriptive matter in which there are illustrated preferred embodiments of the invention.

BRIEF DESCRIPTION OF THE DRAWINGS

The invention will be better understood and embodiments other than those set forth above will become apparent when consideration is given to the following detailed description thereof. Such description makes reference to the annexed drawings wherein.

The same reference numerals refer to the same parts throughout the various Figures.

DETAILED DESCRIPTION OF INVENTION

Figure 1:
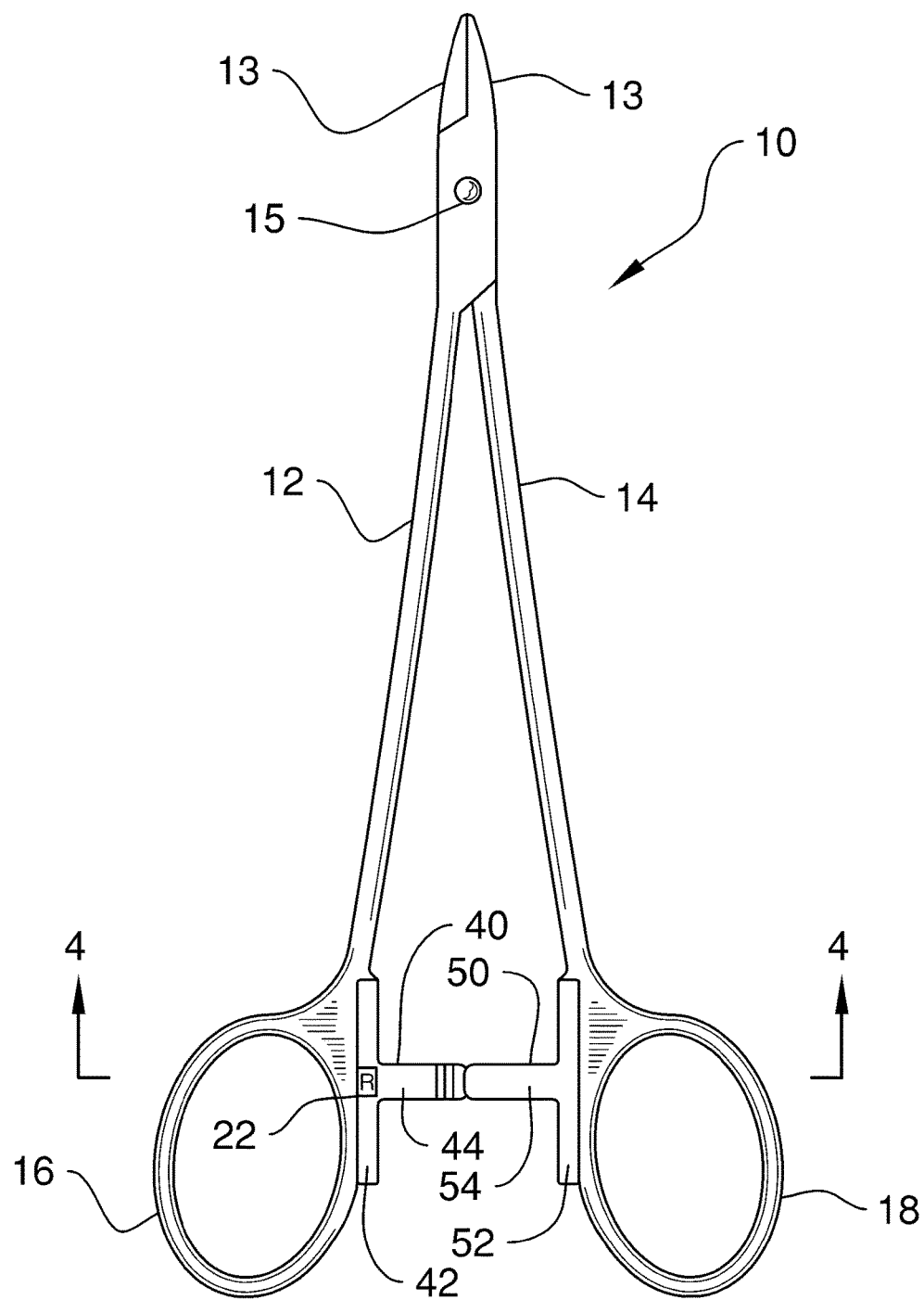
FIG. 1 is a front elevational view of the ambidextrous locking clamp system constructed in accordance with the principles of the present invention.

Referring now to the drawings and particularly to FIGS. 1-33, a first embodiment of the ambidextrous locking clamp system of the present invention is shown and generally designated by the reference numeral 10.

In FIG. 1, a new and improved ambidextrous locking clamp system 10 of the present invention for allowing the use of a hand operated device by a right or left handed user is illustrated and will be described. More particularly, the ambidextrous locking clamp system 10 has a first elongated member 12 and a second elongated member 14 each having a working head 13, wherein the working heads can be, but not limited to, a gripping jaw or a cutting edge. The second elongated member 14 is connected to the first elongated member 12 via a hinge 15. The first and second elongated members 12, 14 each has a corresponding finger engaging member 16, 18 located opposite of their respective working heads 13, wherein each finger engaging member has an indicator 22, 32 for identifying a first and second side of the ambidextrous locking clamp system. Additionally, a first latching member 40 is removably attached to the finger engaging members 16, 18 and a second latching member 50 is removably attached to the finger engaging members 16, 18. The first and second elongated members 12, 14 can be made from any suitable material having reflex memory.

Figure 2:
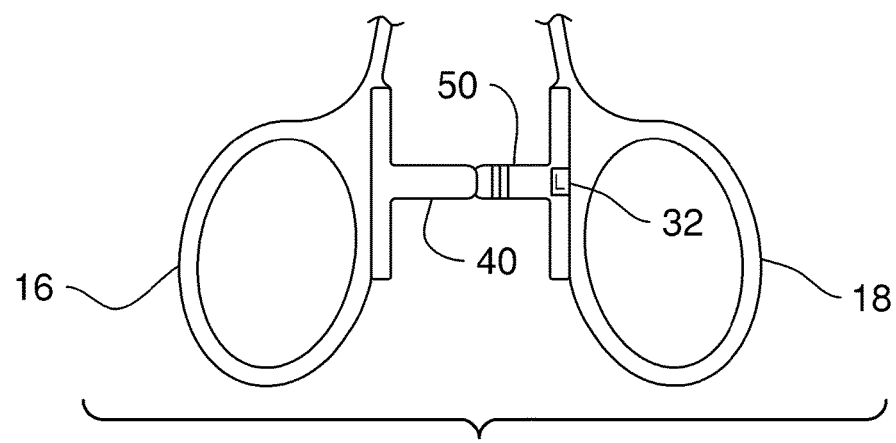
FIG. 2 is an enlarged front elevational view of the ambidextrous locking clamp system in an alternate configuration of the present invention.

The indicators 22, 32 will have a marking or indicia thereon, such as but limited to an "L" and "R" to indicate the configuration of the ambidextrous locking clamp 10. Indicator 22 is located on a protrusion 20 extending out from the first finger engaging member 16, and indicator 32 is located on a protrusion 30 extending out from the second finger engaging member 18. The indicators 22, 32 are intended to separately and independently identify the first and second elongated members 12, 14 of the ambidextrous locking clamp system 10 respectively attached thereon, so a user can distinguish between the left and right, as best illustrated in FIGS. 1 and 2.

Figure 3:
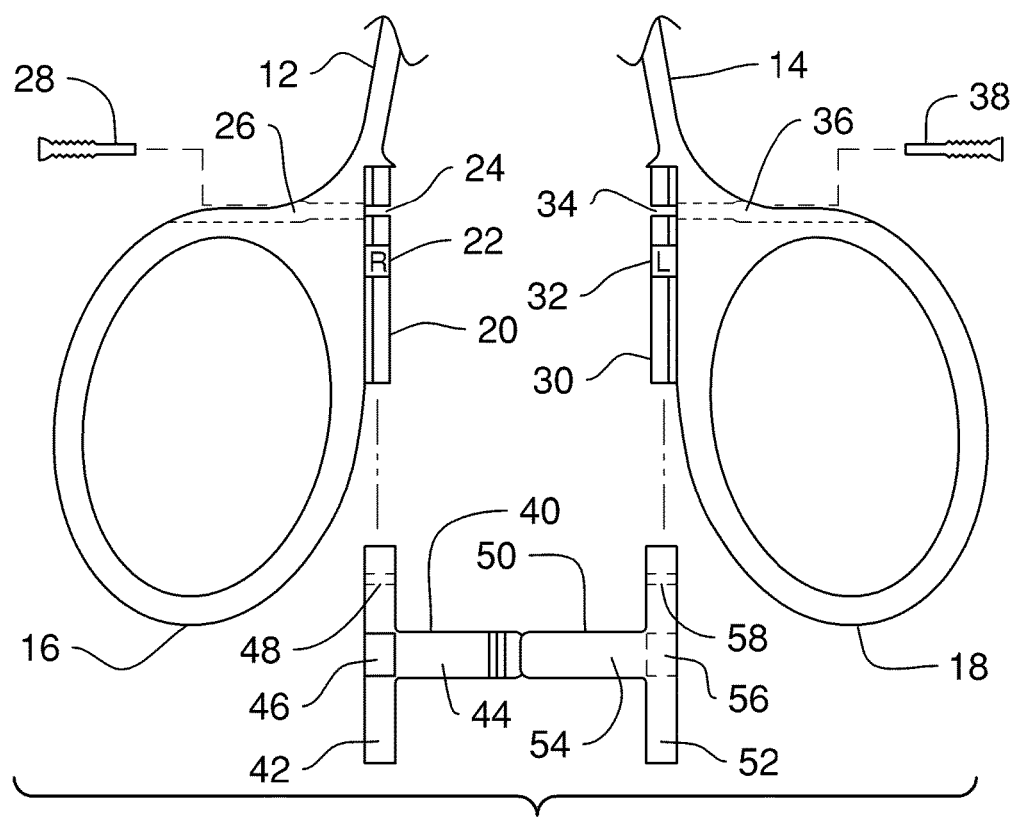
FIG. 3 is an exploded front elevational view of the ambidextrous locking clamp system of the present invention.
Figure 5:
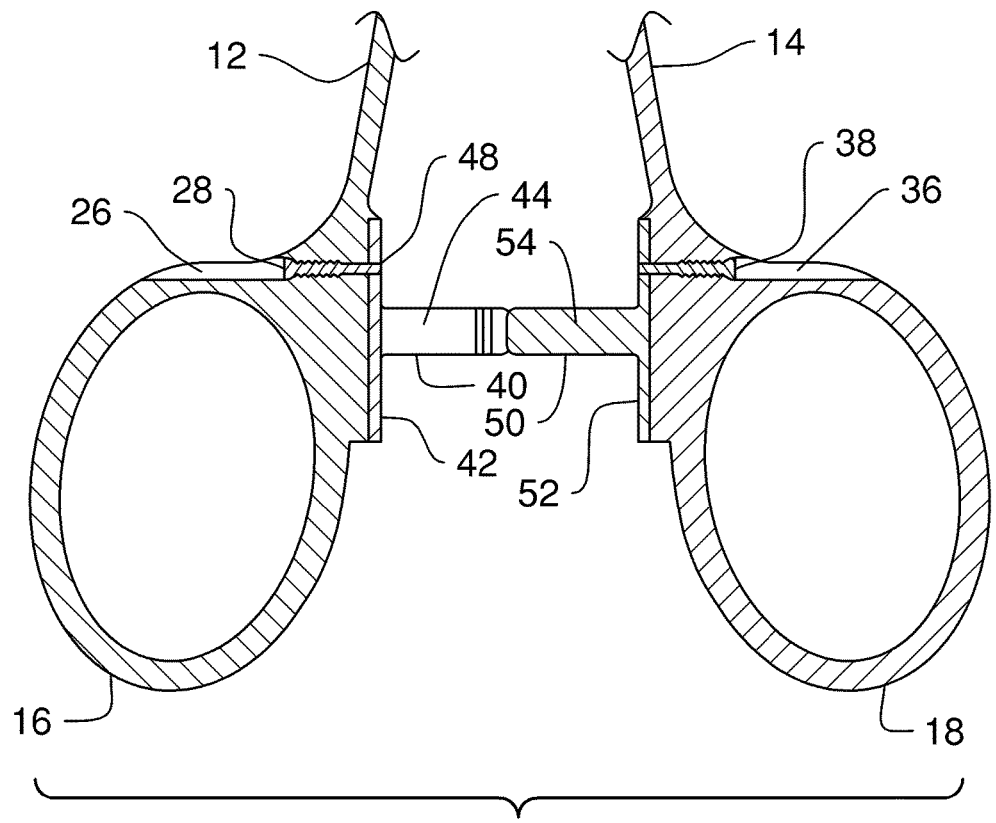
FIG. 5 is a cross-sectional view of the ambidextrous locking clamp system of the present invention taken along cross-section line 5-5 in FIG. 4.

The first and second latching members 40, 50 each have an elongated base 42, 52, a ratcheting head 44, 54 extending out from their respective elongated base, an opening 46, 56 for viewing the indicator 22, 32 therebelow, and an aperture 48, 58 adapted and configured to receive a threaded retaining pin 28, 38. The ratcheting heads 44, 54 are substantially perpendicular to their respective elongated bases 42, 52, thereby forming a generally T-shaped configuration. The retaining pins 28, 38 are securely retained within a bore 26, 36 defined through the finger engaging members 16, 18, and also extend through the apertures 48, 58 thereby prevent the latching members 40, 50 from being removed from their respective protrusions 20, 30. The bores 26, 36 can be partially or completely threaded so as to threadably receive the retaining pins 28, 38, as best illustrated in FIGS. 3 and 5. The retaining pins 28, 38 can each have a non-threaded tip configured to be received through the apertures 48, 58 of the latching members 40, 50. The ratcheting heads 44, 54 feature a plurality of teeth thereon, which are adapted to join and lock together when engaged by squeezing the finger engaging members 16, 18 together. The teeth are able to disengage when pulled apart by the flexing of the first and second elongated members 12, 14 when an opposing force is applied to the finger engaging members 16, 18.

Figure 4:
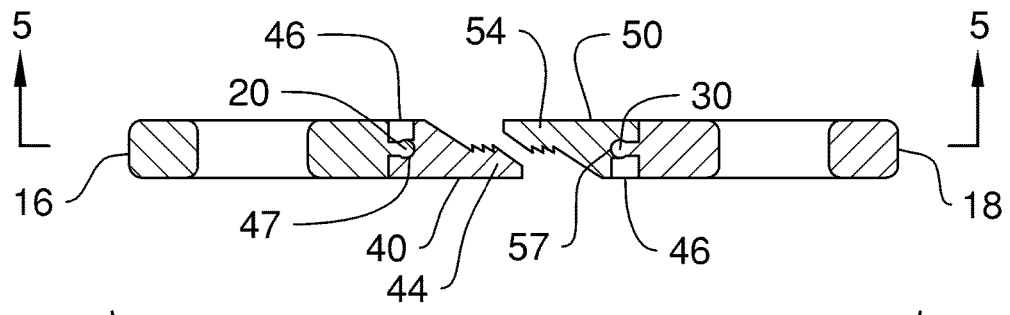
FIG. 4 is a cross-sectional view of the ambidextrous locking clamp system of the present invention taken along cross-section line 4-4 in FIG. 1.

The protrusion 20 features a notch 24 aligned with the bore 26. The bore 26 and the notch 24 are adapted and configured to receive the retaining pin 28, 38 therethrough. The retaining pin 28 is threaded and has a non-threaded tip, wherein the tip is adapted to be received through the notch 24. The protrusion 20 is adapted to slidably receive latching members 40, 50. The protrusion 30 features a notch 34 aligned with the bore 36. The bore 36 and the notch 34 are adapted and configured to receive the retaining pin 28, 38 therethrough. The retaining pin 38 is threaded and has a non-threaded tip, wherein the tip is adapted to be received through the notch 34. The protrusion 30 is adapted to slidably receive latching members 40, 50. FIG. 3 is an exploded view best illustrating the above configuration. It can be appreciated that retaining pins 28, 38 are identical and interchangeable The elongated base 42, 52 of the first and second latching members 40, 50 each have a channel 47, 57 running the length of the elongated base. The channels 47, 57 are adapted and configured to slide on and be retained by the protrusions 20, 30 extending out from the finger engaging members 16, 18. The configuration of the channels 47, 57 and the protrusions 20, 30 allow the first and second latching members 40, 50 to slide over the protrusion, but at the same time not allowing the latching members to be pulled off the protrusions in a direction perpendicular to the sliding motion. FIGS. 4 and 5 best illustrate one possible example of the channel and protrusion configuration.

The first and second latching members 40, 50 are symmetrical so that they may be removed, inverted and then replaced, thereby changing the orientation of the latching members and allowing a right or left handed user to operate the device 10. Furthermore, other configurations of the first and second latching members 40, 50 maybe used in place of the above described latching members.

Figure 6:
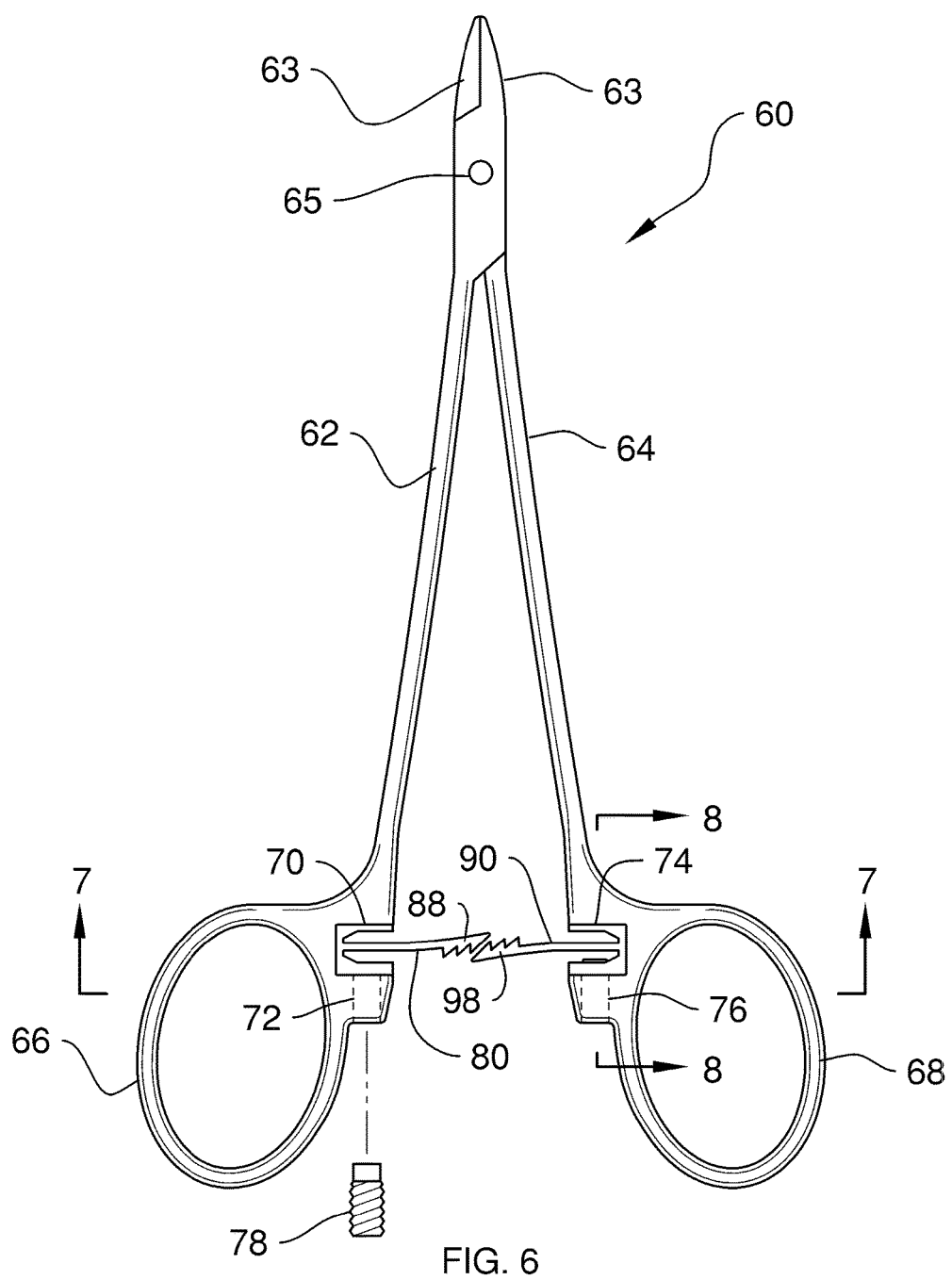
FIG. 6 is a front elevational view of a second alternate embodiment of the ambidextrous locking clamp system of the present invention.

Referring now to FIG. 6, a second alternate embodiment of the ambidextrous locking clamp system of the present invention is shown and generally designated by the reference numeral 60. More particularly, the ambidextrous locking clamp system 60 has a first elongated member 62 and a second elongated member 64 each having a working head 63, wherein the working heads can be, but not limited to, a gripping jaw or a cutting edge. The second elongated member 64 is connected to the first elongate member 62 via a hinge 65. The first and second elongated members 62, 64 each have a corresponding finger engaging member 66, 68 located opposite of their respective working heads 63. A first latching member 80 and a second latching member 90 are interchangeably and slidably received in a notch 70 located in the first finger engaging member 66, and in a notch 74 located in the second finger engaging member 68. The notches 70, 74 are orientated so as to face each other. Additionally, a retaining pin 78 is used to secure the latching members 80, 90 in their respective notches 70, 74, through a threaded bore 72 located adjacent the notch 70 and a threaded bore 76 located adjacent the notch 74. The threaded bores 72, 76 are substantially perpendicular with their respective adjacent notches 70, 74. The threaded bores 72, 76 are in communication with their respective notches 70, 74.

Figure 7:
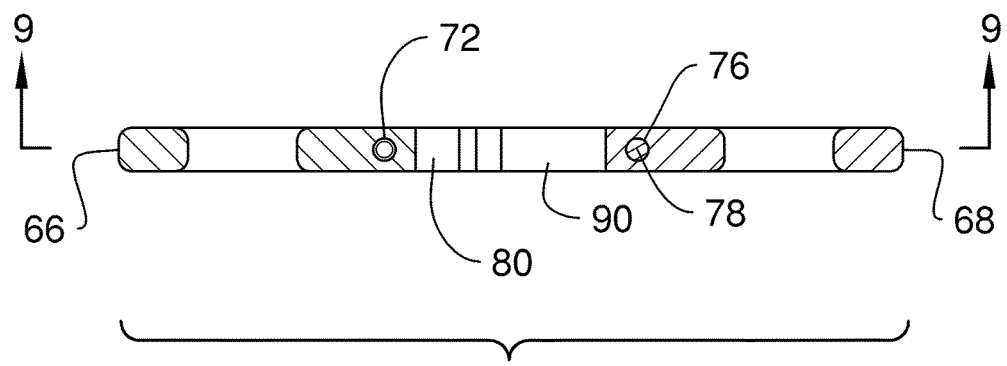
FIG. 7 is an enlarged cross-sectional view of the second alternate embodiment of the present invention taken along cross-section line 7-7 in FIG. 6.

FIG. 7 illustrates the bore 72 without the retaining pin, while bore 76 has the retaining pin 78 therein.

Figure 8:
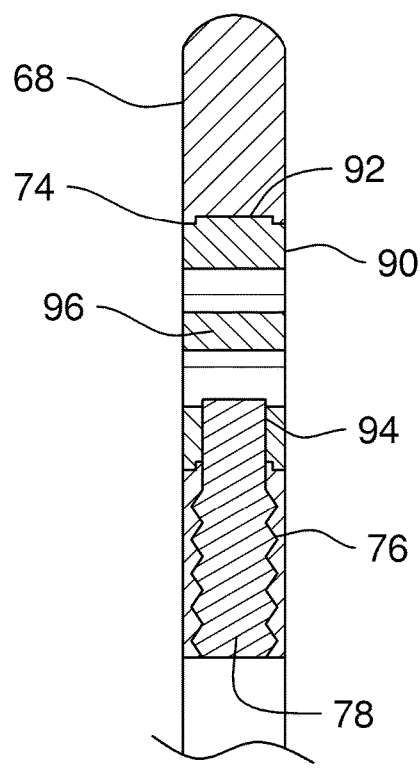
FIG. 8 is an enlarged cross-sectional view of the second alternate embodiment of the present invention taken along cross-section line 8-8 in FIG. 6.

It should be understood that only finger engaging member 68 is shown in FIG. 8 and described herewith, and that latching members 80, 90 can be used with either finger engaging members 66, 68. The latching member 90 features a detent 92 on a first side of the latching member that corresponds to a top side of the notch 74. The detent 92 protrudes into the corresponding top side of the notch 74, allowing the first and second latching members 80, 90 to slide in the notch 74, but at the same time not allowing the latching members to be pulled out of the notch 74 in a direction perpendicular to the sliding motion. FIG. 8 also illustrates the retaining pin 78 threadably retained in the threaded bore 76. The retaining pin 78 has a non-threaded tip which is received within an aperture 94 located through a second side of the latching member 90 opposite the detent 92. The retaining pin 78 secures the latching member 90 in the notch 74, preventing the latching member from being removed from the slot. The second side of the latch member 90 is configured to receive a detent protruding from a bottom side of the notch 74.

Figure 9:
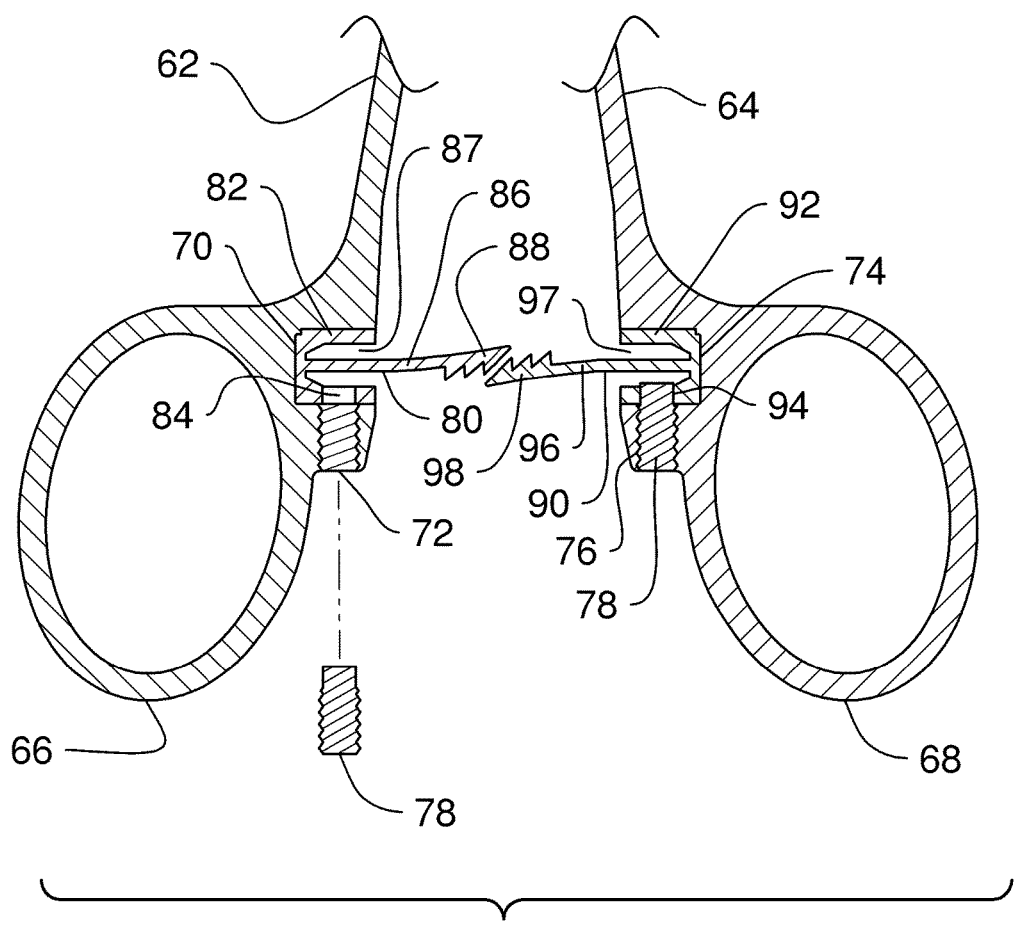
FIG. 9 is an enlarged cross-sectional view of the second alternate embodiment of the present invention taken along cross-section line 9-9 in FIG. 7.

FIG. 9 best illustrates one possible configuration of the first and second latching members 80, 90 in relation to their respective finger engaging members 66, 68. The first latching member 80 has an elongated flexible arm 86 with a ratcheting head 88 featuring a plurality of ratcheting teeth thereon, a detent 82, and an aperture 84. The detent 82 protrudes into a corresponding top side of notch 70, 74, as described above. The aperture 84 is located on a second side opposite the detent 82 and is aligned with the threaded bore 72, 76 when positioned in its respective notch 70, 74. The aperture 84 is adapted to receive the tip of the retaining pin 78 therethrough or therein when the retaining pin is threaded in the bore 72, 76. The flexible arm 86 is positioned between the detent 82 and the aperture 84 sides of the latching member 80 so as to extend through a first latching member notch 87 defined in the first latching member 80 between the detent 82 and the aperture 84 sides.

The second latching member 90 has an elongated flexible arm 96 with a ratcheting head 98 featuring a plurality of teeth thereon, the detent 92, and the aperture 94. The detent 92 protrudes into a corresponding top side of notch 70, 74, as described above. The aperture 94 is located opposite the detent 92 and is aligned with the threaded bore 72, 76 when positioned in its respective notch 70, 74. The aperture 94 is adapted to receive the tip of the retaining pin 78 therethrough or therein when the retaining pin is threaded in the bore 72, 76. The flexible arm 96 is positioned between the detent 92 and the aperture 94 sides of the latching member 90 so as to extend through a second latching member notch 97 defined in the second latching member 90 between the detent 92 and the aperture 94 sides. The ratcheting heads 88, 98 are adapted to join and lock together when engaged by squeezing the finger engaging members 66, 68 together. The teeth are able to disengage when pulled apart by flexing the first and second elongated members 62, 64 when an opposing perpendicular force in either direction is applied to the finger engaging members 66, 68 by pushing with the thumb and pulling with the fingers of the operating hand thereby separating the parallel engaged teeth.

It can be appreciated that retaining pins 78 are identical and interchangeable, and that the first and second latching members 80, 90 are interchangeable with notches 70, 74. It can also be appreciated that the ambidextrous locking clamp system 60 can be used with either the left or right hand with identical methods of separating and disengaging the teeth of ratcheting heads 88, 98.

The first and second latching members 80, 90 are symmetrical so that they may be removed and interchanged with each other, and then replaced, thereby changing the orientation of the latching members of device 60.

Figure 10:
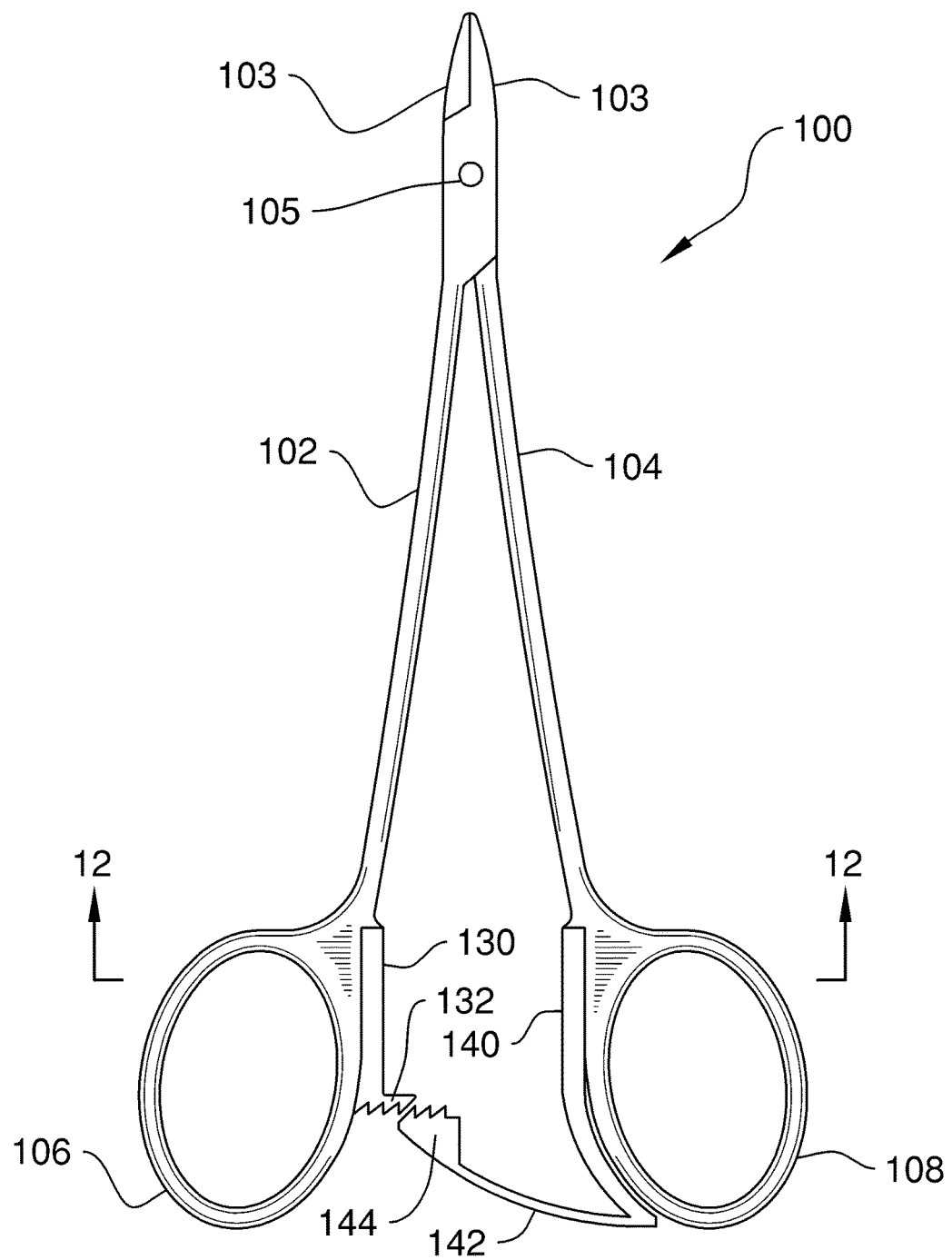
FIG. 10 is a front elevational view of a third alternate embodiment of the ambidextrous locking clamp system of the present invention.

Referring now to FIG. 10, a third alternate embodiment of the ambidextrous locking clamp system of the present invention is shown and generally designated by the reference numeral 100. More particularly, the ambidextrous locking clamp system 100 has a first elongated member 102 and a second elongated member 104 each having a working head 103, wherein the working heads can be, but not limited to, a gripping jaw or a cutting edge. The second elongated member 104 is connected to the first elongate member 102 via a hinge 105. The first and second elongated members 102, 104 have a corresponding finger engaging member 106, 108 located opposite of the working heads 103, wherein each finger engaging member can slidably receive a first latching member 130 or a second latching member 140. The first latching member 130 has a ratcheting head 132 featuring ratcheting teeth thereon, and the second latching member 140 has a flexible arm 142 extending out therefrom, and a ratcheting head 144 located at the free end of the flexible arm 142. The ratcheting head 144 features ratcheting teeth thereon adapted to engage with the ratcheting teeth of the ratcheting head 132.

Figure 11:
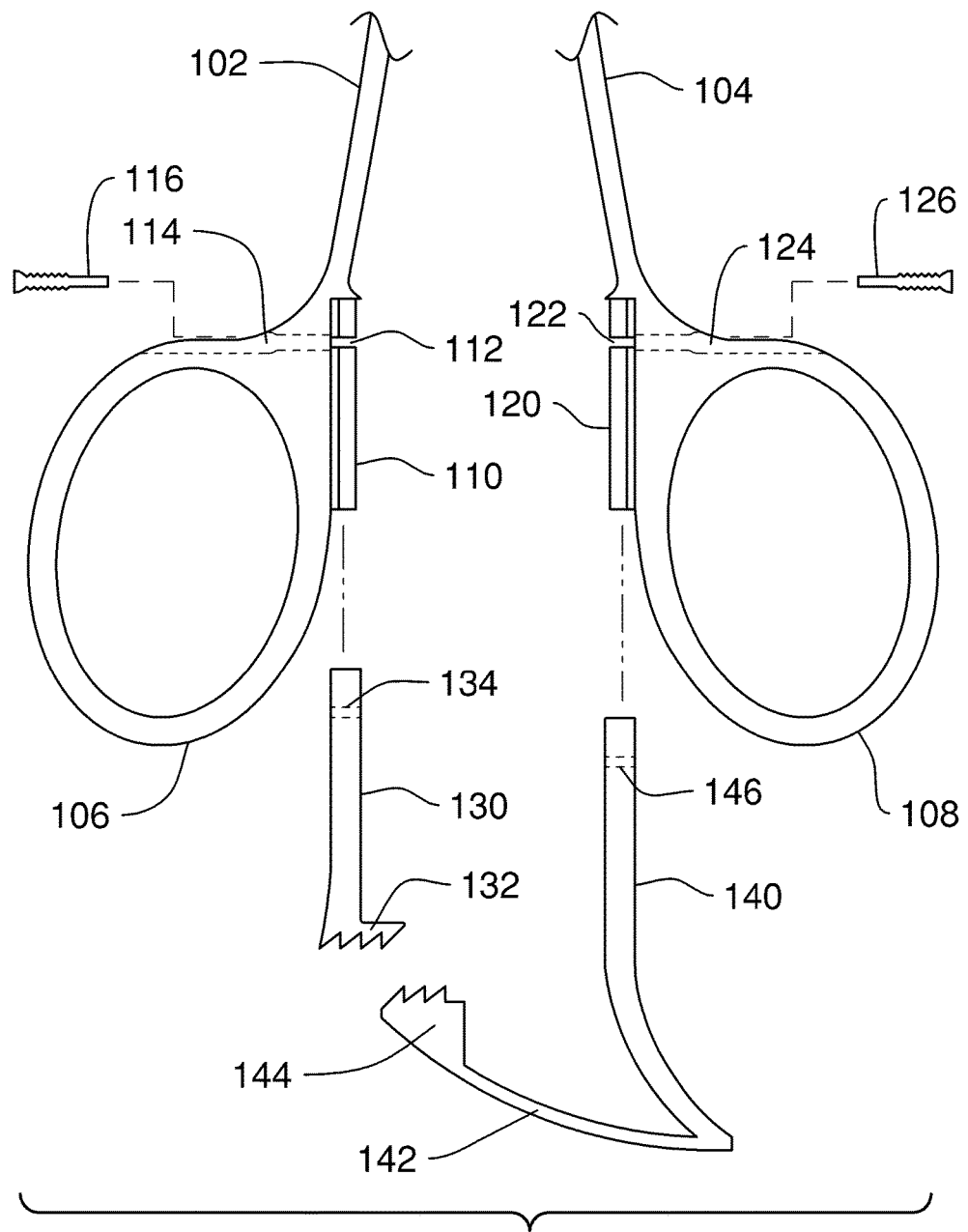
FIG. 11 is an exploded front elevational view of the third alternate embodiment of the ambidextrous locking clamp system of the present invention.

The finger engaging member 106 has a threaded bore 114, and a protrusion 110 extending out from the finger engaging member 106 perpendicular to the threaded bore 114. The protrusion 110 features a notch 112 aligned with the bore 114. The bore 114 and the notch 112 are adapted and configured to receive a retaining pin 116 therethrough. The retaining pin 116 is threaded and has a non-threaded tip, wherein the tip is adapted to be received through the notch 112. The protrusion 110 is adapted to slidably receive latching members 130, 140. The finger engaging member 108 has a threaded bore 124, and a protrusion 120 extending out from the finger engaging member 108 perpendicular to the threaded bore 124. The protrusion 120 features a notch 122 aligned with the bore 124. The bore 124 and the notch 122 are adapted and configured to receive a retaining pin 126 therethrough. The retaining pin 126 is threaded and has a non-threaded tip, wherein the tip is adapted to be received through the notch 122. The protrusion 120 is adapted to slidably receive latching members 130, 140. It can be appreciated that retaining pins 116, 126 are identical and interchangeable. FIG. 11 is an exploded view best illustrating the above configuration.

Figure 12:
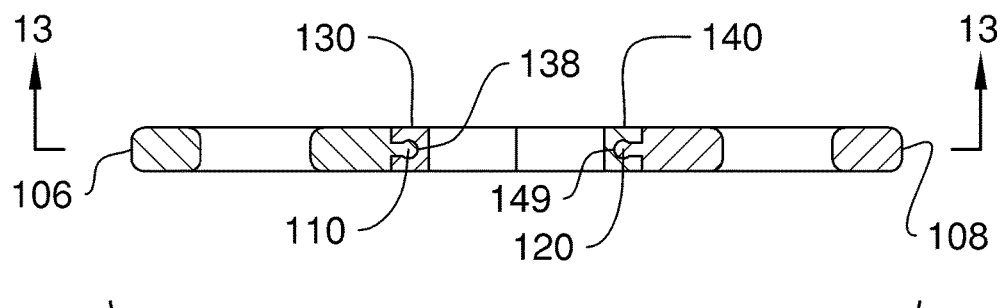
FIG. 12 is an enlarged cross-sectional view of the third alternate embodiment of the present invention taken along cross-section line 12-12 in FIG. 10.

The latching members 130, 140 each have a channel 138, 149 running the length of their respective latching members. The channels 138, 149 are adapted and configured to slide on and be retained by the protrusions 110, 120 extending out from their respective finger engaging members 106, 108. The configuration of the channels 138, 149 and the protrusions 110, 120 allow the latching members 130, 140 to slide over the protrusion, but at the same time not allowing the latching members to be pulled off the protrusions in a direction perpendicular to the sliding motion. FIG. 12 best illustrates one possible example of the channel and protrusion configuration.

Figure 13:
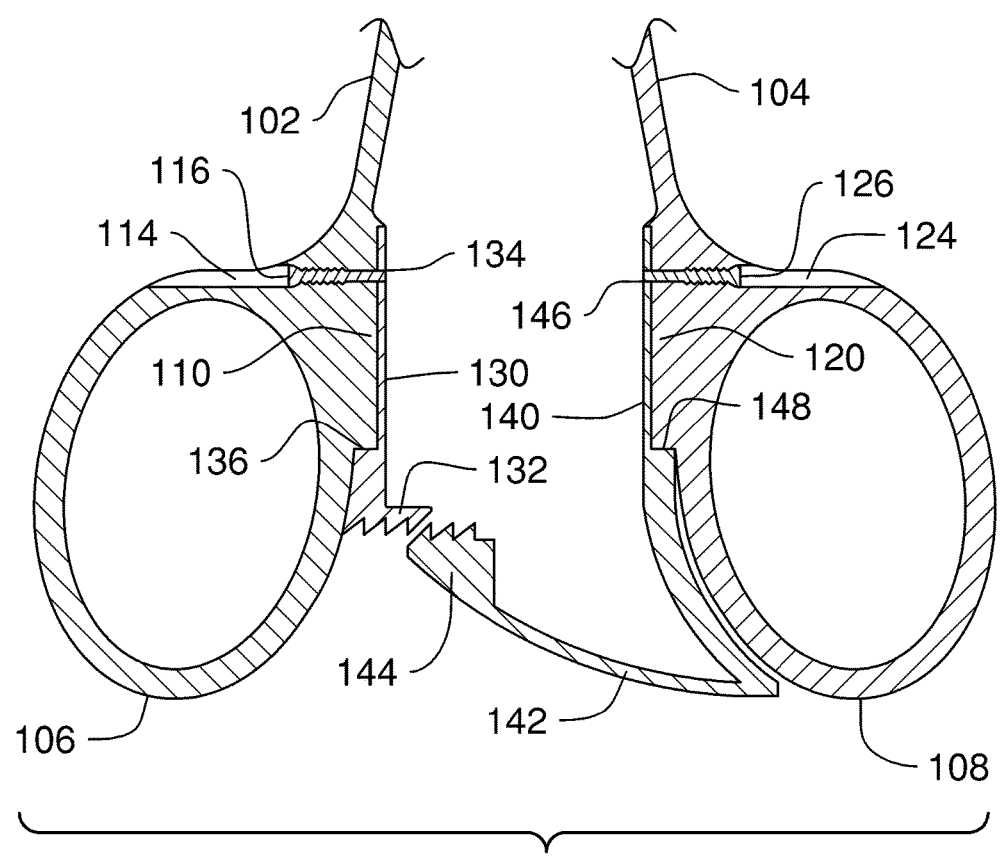
FIG. 13 is an enlarged cross-sectional view of the third alternate embodiment of the present invention taken along cross-section line 13-13 in FIG. 12.

FIG. 13 best illustrates one possible configuration of the first and second latching members 130, 140 in relation to their respective finger engaging members 106, 108. The first latching member 130 has the ratcheting head 132 featuring a plurality of ratcheting teeth thereon, a stop 136, and an aperture 134. The stop 136 is perpendicular to the longitudinal axis of the latching member 130 and it is adapted to abut against a free end of it respective protrusion 110, 120. The aperture 134 is located opposite the stop 136 and is aligned with the threaded bore 114, 124 and the notch 112, 122 when positioned on its respective protrusion 110, 120. The aperture 134 is adapted to receive the tip of the retaining pin 116, 126 therethrough or therein when the retaining pin is threaded in the bore 114, 124, through notch 112, 122, and through aperture 134. The second latching member 140 has the flexible arm 142, the ratcheting head 144 featuring a plurality of ratcheting teeth thereon, a stop 148, and an aperture 146. The stop 148 is perpendicular to the longitudinal axis of the latching member 140 and it is adapted to abut against a free end of it respective protrusion 110, 120. The aperture 146 is located opposite the stop 148 and is aligned with the threaded bore 114, 124 and the notch 112, 122 when positioned on its respective protrusion 110, 120. The aperture 146 is adapted to receive the tip of the retaining pin 116, 126 therethrough or therein when the retaining pin is threaded in the bore 114, 124, and through notch 112, 122 and aperture 146. The flexible arm 142 extends out from a section of the latching member 140 extending past the ratcheting head 132 of the first latching member 130, when both latching members 130, 140 are attached to their respective protrusions 110, 120. The flexible arm 142 has a generally arcuate shape curving upwardly toward the ratcheting head 132 of the first latching member 130. This extension of the second latching member 140 has a shape that corresponds to the shape of the finger engaging member 106, 108. The ratcheting head 144 is attached to the free end of the flexible arm 142, thereby allowing the ratcheting head 144 to free travel with the flexing of the flexible arm 142. The ratcheting heads 132, 144 are adapted to join and lock together when engaged by squeezing the finger engaging members 106, 108 together. The teeth are able to disengage when pulled apart by flexing the first and second elongated members 102, 104 when an opposing perpendicular force is applied to the finger engaging members 106, 108 by pushing with the thumb and pulling with the fingers of the operating hand thereby separating the parallel engaged teeth.

It can be appreciated that retaining pins 116, 126 are identical and interchangeable, and that the channels 138, 149 of first and second latching members 130, 140 are identical interchangeable with protrusions 110, 120. It can also be appreciated that the ambidextrous locking clamp system 100 can be used with either the left or right hand with identical methods of separating and disengaging the teeth of ratcheting heads 132, 144.

The channels 138, 149, apertures 134, 146, and stop 136, 148 of the first and second latching members 130, 140 are symmetrical so that they may be removed, inverted and then replaced, thereby changing the orientation of the latching members of device 100. Furthermore, other configurations of the first and second latching members 130, 140 may be used in place of the above described latching members.

Figure 14:
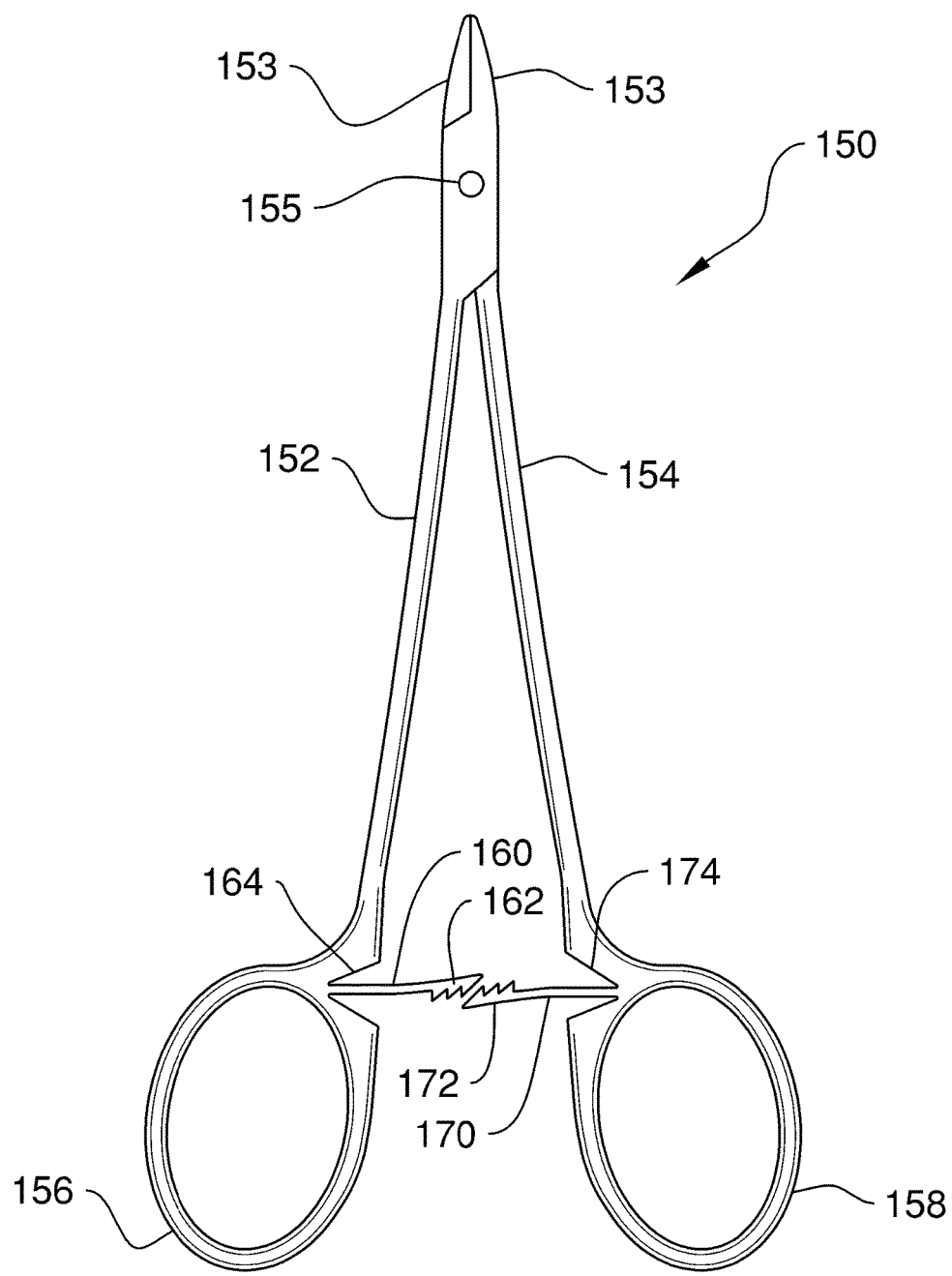
FIG. 14 is a front elevational view of a fourth alternate embodiment of the present invention.

Referring now to FIG. 14, a fourth alternate embodiment of the ambidextrous locking clamp system of the present invention is shown and generally designated by the reference numeral 150. More particularly, the ambidextrous locking clamp system 150 has a first elongated member 152 and a second elongated member 154 each having a working head 153, wherein the working heads can be, but not limited to, a gripping jaw or a cutting edge. The second elongated member 154 is connected to the first elongate member 152 via a hinge 155. The first and second elongated members 152, 154 each have a corresponding finger engaging member 156, 158 located opposite of their respective working heads 153. The first finger engaging member 156 has a latching member 160 extending out from a notch 164, and a ratcheting head 162 located at the free end of the latching member 160. The ratcheting head 162 features ratcheting teeth thereon. The second finger engaging member 158 has a latching member 170 extending out from a notch 174, and a ratcheting head 172 located at the free end of the latching member 170. The ratcheting head 172 features ratcheting teeth thereon adapted to engage with the ratcheting teeth of the ratcheting head 162 when the first and second finger engaging members 156, 158 are squeezed together.

Figure 15:
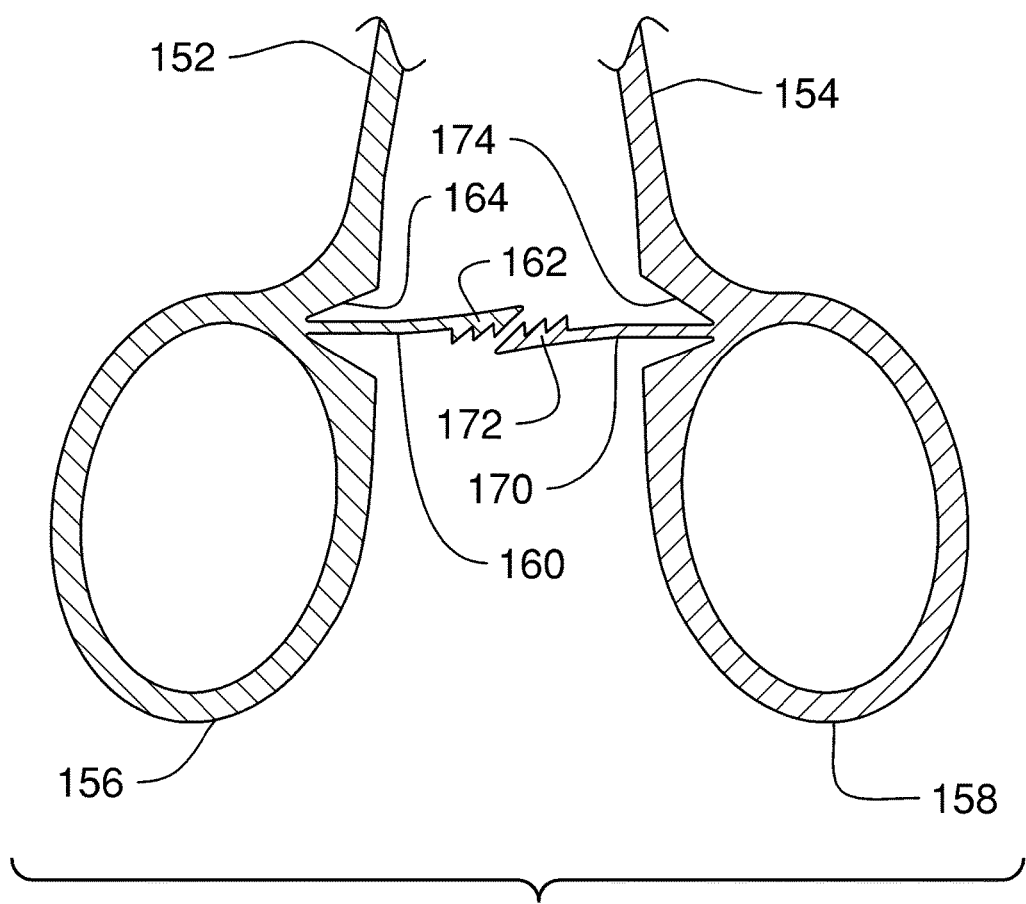
FIG. 15 is an enlarged cross-sectional view of the fourth alternate embodiment of the present invention of FIG. 14.

As illustrated in FIG. 15, the first and second finger engaging members 156, 158, the latching members 160, 170, and the notches 164, 174 are symmetrical and mirror images of each other. The latching member 160 of the first finger engaging member 156 is a flexible arm that extends out from the notch 164 toward the second finger engaging member 158. The notch 164 can have any geometric shape, but preferably a V-shape with the latching member 160 extending out from the central interior of the V-shaped notch. The latching member 170 of the second finger engaging member 158 is a flexible arm that extends out from the notch 174 toward the first finger engaging member 156. The notch 174 can have any geometric shape, but preferably a V-shape with the latching member 170 extending out from the central interior of the V-shaped notch.

The ratcheting heads 162, 172 are adapted to join and lock together when engaged by squeezing the finger engaging members 156, 158 together. The teeth are able to disengage when pulled apart by flexing the first and second elongated members 152, 154 when an opposing force is applied to the finger engaging members 156, 158 in a perpendicular movement in either direction by pushing with the thumb and pulling with the fingers of the operating hand thereby separating the parallel engaged teeth.

It can be appreciated that the ambidextrous locking clamp system 150 can be used with either the left or right hand with identical methods of separating and disengaging the teeth of ratcheting heads 162, 172 and/or with the flexing of the elongated members in a perpendicular movement in either direction.

Figure 16:
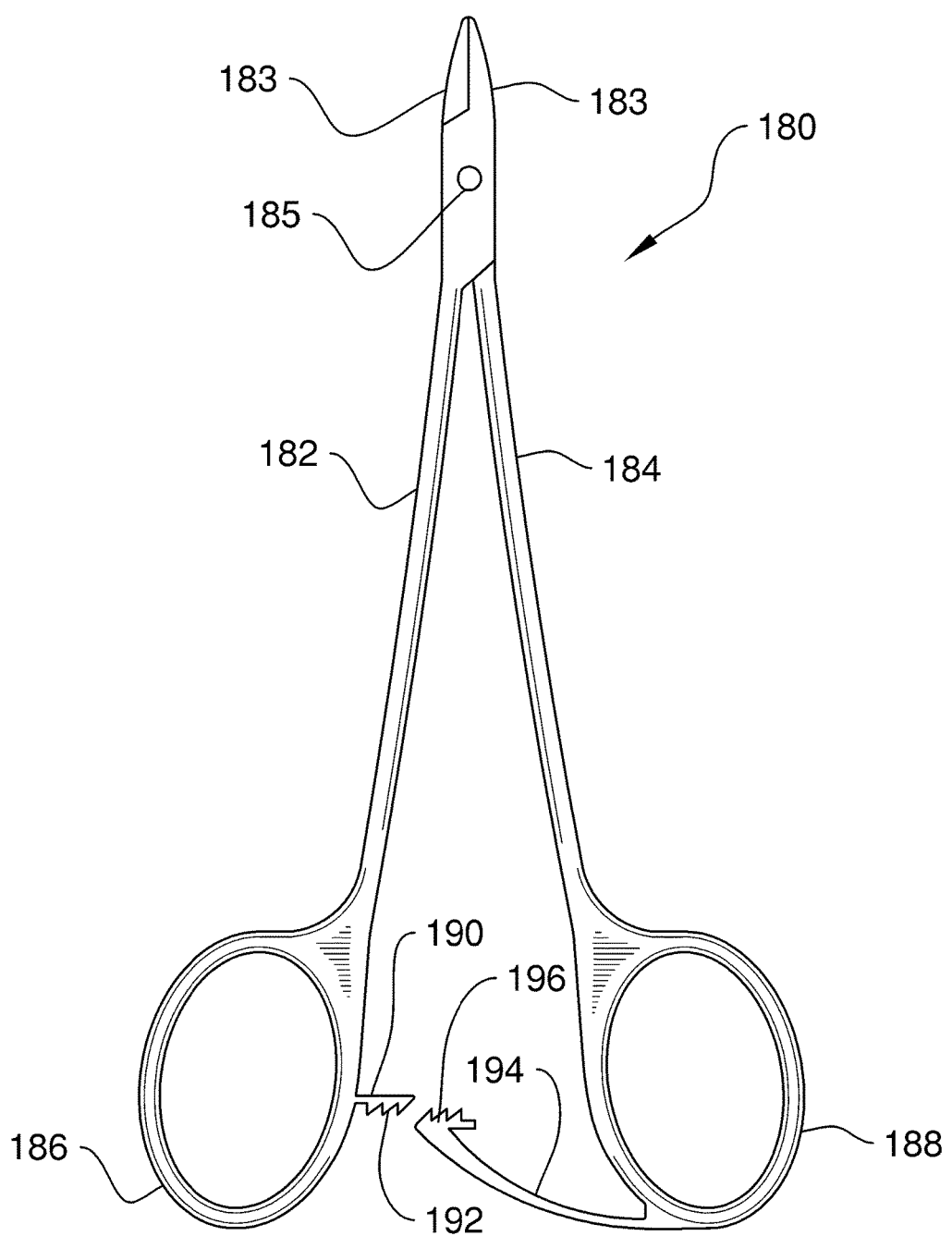
FIG. 16 is a front elevational view of a fifth alternate embodiment of the present invention.

Referring now to FIG. 16, a fifth alternate embodiment of the ambidextrous locking clamp system of the present invention is shown and generally designated by the reference numeral 180. More particularly, the ambidextrous locking clamp system 180 has a first elongated member 182 and a second elongated member 184 each having a working head 183, wherein the working heads can be, but not limited to, a gripping jaw or a cutting edge. The second elongated member 184 is connected to the first elongate member 182 via a hinge 185. The first and second elongated members 182, 184 each have a corresponding finger engaging member 186, 188 located opposite of their respective working heads 183. The first finger engaging member 186 has a latching member 190 extending out therefrom, and a ratcheting head 192 located at the free end of the latching member 190. The ratcheting head 192 features ratcheting teeth thereon. The second finger engaging member 188 has a latching member 194 extending out therefrom, and a ratcheting head 196 located at the free end of the latching member 194. The ratcheting head 196 features ratcheting teeth thereon adapted to engage with the ratcheting teeth of the ratcheting head 192 when the first and second finger engaging members 186, 188 are squeezed together.

Figure 17:
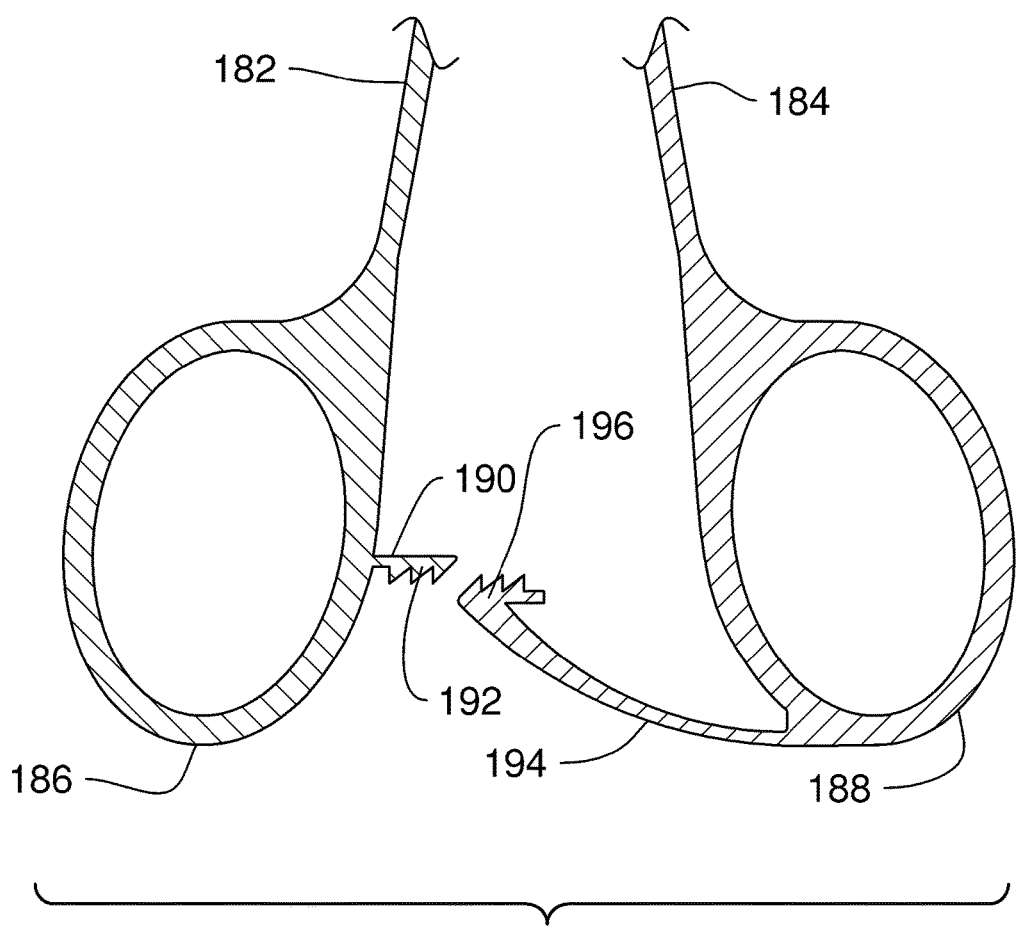
FIG. 17 is an enlarged cross-sectional view of the fifth alternate embodiment of the present invention of FIG. 16.

As illustrated in FIG. 17, the latching member 190 of the first finger engaging member 186 extends out from the interior of the first finger engaging member toward the second finger engaging member 188. The latching member 194 of the second finger engaging member 188 is a flexible arm that extends outwardly and upwardly from the bottom of the second finger engaging member 188 and below the latching member 190 toward the first finger engaging member 186. The ratcheting head 196 is located on the free end of the flexible arm latching member 194. The flexible arm latching member 194 tapers with the thickest part being attached to the ratcheting head and the thinnest part being attached to the bottom of the second finger engaging member 188, and has a generally arcuate shape. Thereby allowing the latching member 194 to have a more degree of flexibility at its second finger engaging member attachment point, and increasing the travel length of ratcheting head 196.

The ratcheting heads 192, 196 are adapted to join and lock together when engaged by squeezing the finger engaging members 186, 188 together. The teeth are able to disengage when pulled apart by flexing the first and second elongated members 182, 184 when an opposing force is applied to the finger engaging members 186, 188 by pushing with the thumb and pulling with the fingers of the operating hand thereby separating the parallel engaged teeth.

It can be appreciated that the ambidextrous locking clamp system 180 can be used with either the left or right hand with identical methods of separating and disengaging the teeth of ratcheting heads 192, 196.

Figure 18:
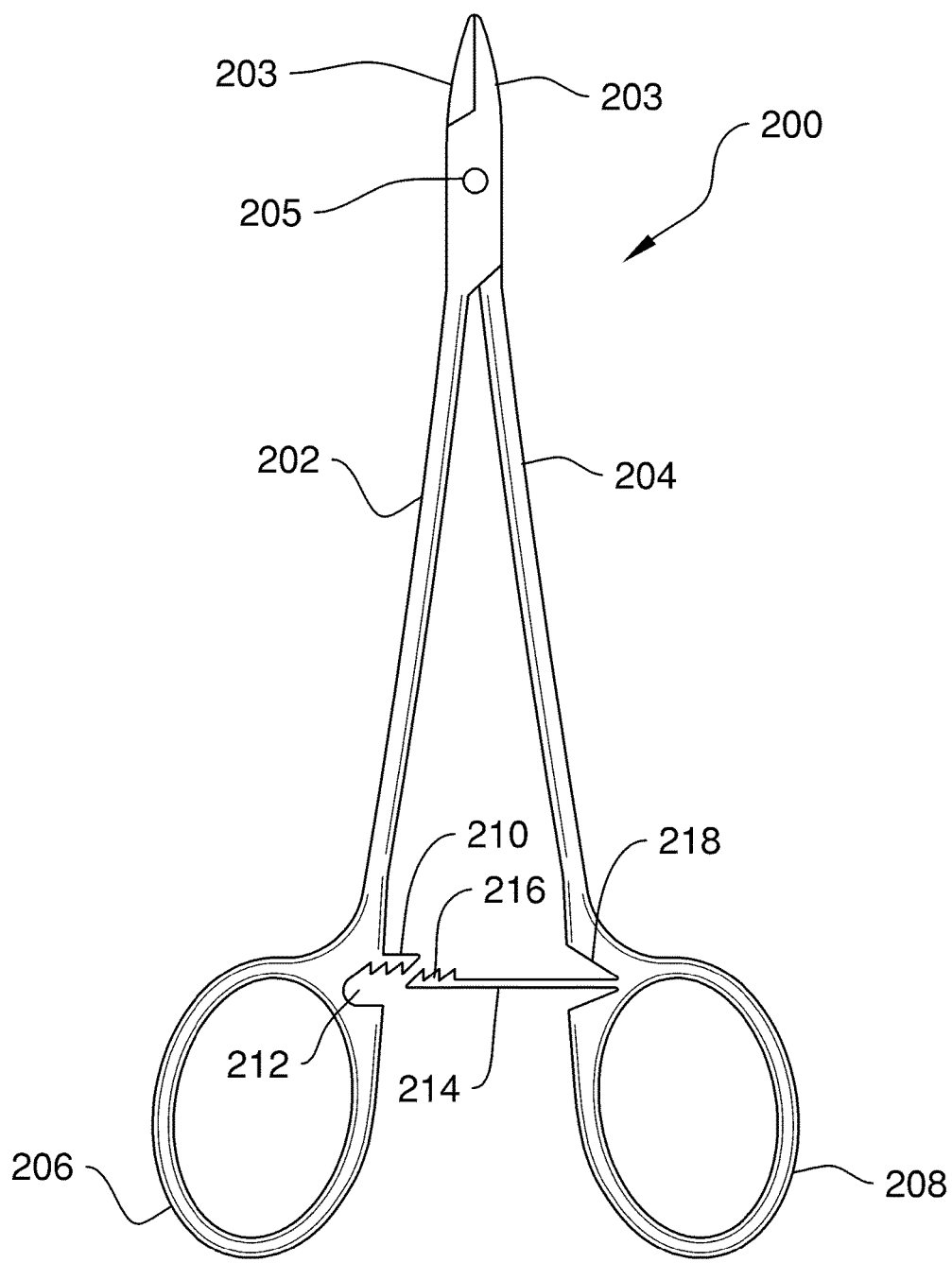
FIG. 18 is a front elevational view of a sixth alternate embodiment of the present invention.

Referring now to FIG. 18, a sixth alternate embodiment of the ambidextrous locking clamp system of the present invention is shown and generally designated by the reference numeral 200. More particularly, the ambidextrous locking clamp system 200 has a first elongated member 202 and a second elongated member 204 each having a working head 203, wherein the working heads can be, but not limited to, a gripping jaw or a cutting edge. The second elongated member 204 is connected to the first elongate member 202 via a hinge 205. The first and second elongated members 202, 204 each have a corresponding finger engaging member 206, 208 located opposite of their respective working heads 203. The first finger engaging member 206 has a latching member 210 extending out therefrom, and a notch 212 adjacent the latching member 210. The latching member 210 features ratcheting teeth thereon. The second finger engaging member 208 has a latching member 214 extending out from a notch 218, and a ratcheting head 216 located at the free end of the latching member 214. The ratcheting head 216 features ratcheting teeth thereon adapted to engage with the ratcheting teeth of the latching member 210 when the first and second finger engaging members 206, 208 are squeezed together.

Figure 19:
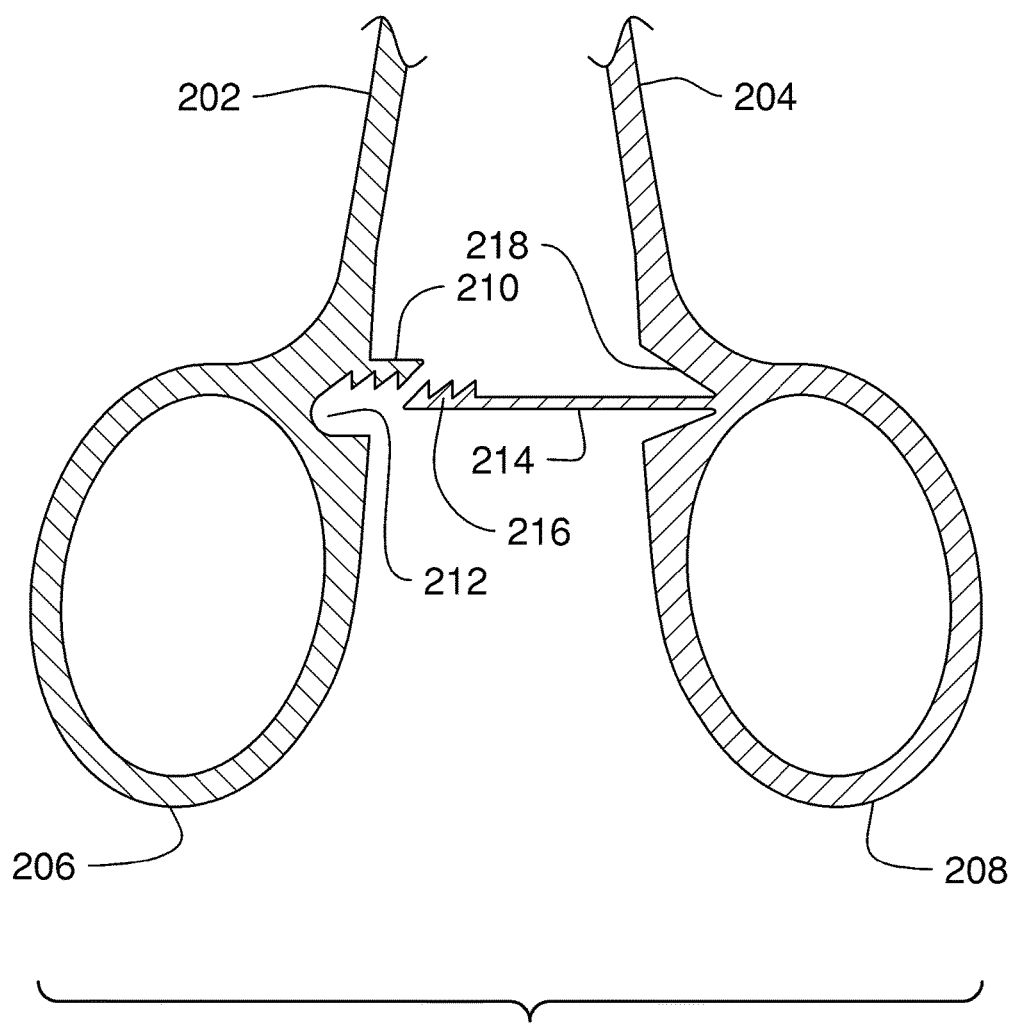
FIG. 19 is an enlarged cross-sectional view of the sixth alternate embodiment of the present invention of FIG. 18.

As illustrated in FIG. 19, the latching member 210 of the first finger engaging member 206 extends out from the first finger engaging member toward the second finger engaging member 208. The notch 212 can have any geometric shape, but preferably a U-shape with the latching member 210 being positioned directly above or below and adjacent to the U-shaped notch. The notch 212 being configured to receive the ratcheting head 216 of the latching member 214 of the second finger engaging member 208, and allowing for the ratcheting head 216 to disengage from the first latching member 210. The latching member 214 of the second finger engaging member 208 is a flexible arm that extends out from the notch 218 toward the first finger engaging member 206. The notch 218 can have any geometric shape, but preferably a V-shape with the latching member 214 extending out from the central interior of the V-shaped notch.

The ratcheting head 216 and the ratcheting teeth of the latching member 210 are adapted to join and lock together when engaged by squeezing the finger engaging members 206, 208 together. The teeth are able to disengage when pulled apart by flexing the first and second elongated members 202, 204 when an opposing force is applied to the finger engaging members 206, 208 by pushing with the thumb and pulling with the fingers of the operating hand thereby separating the parallel engaged teeth.

It can be appreciated that the ambidextrous locking clamp system 200 can be used with either the left or right hand with identical methods of separating and disengaging the teeth of the first latching member 210 and ratcheting head 216.

Figure 20:
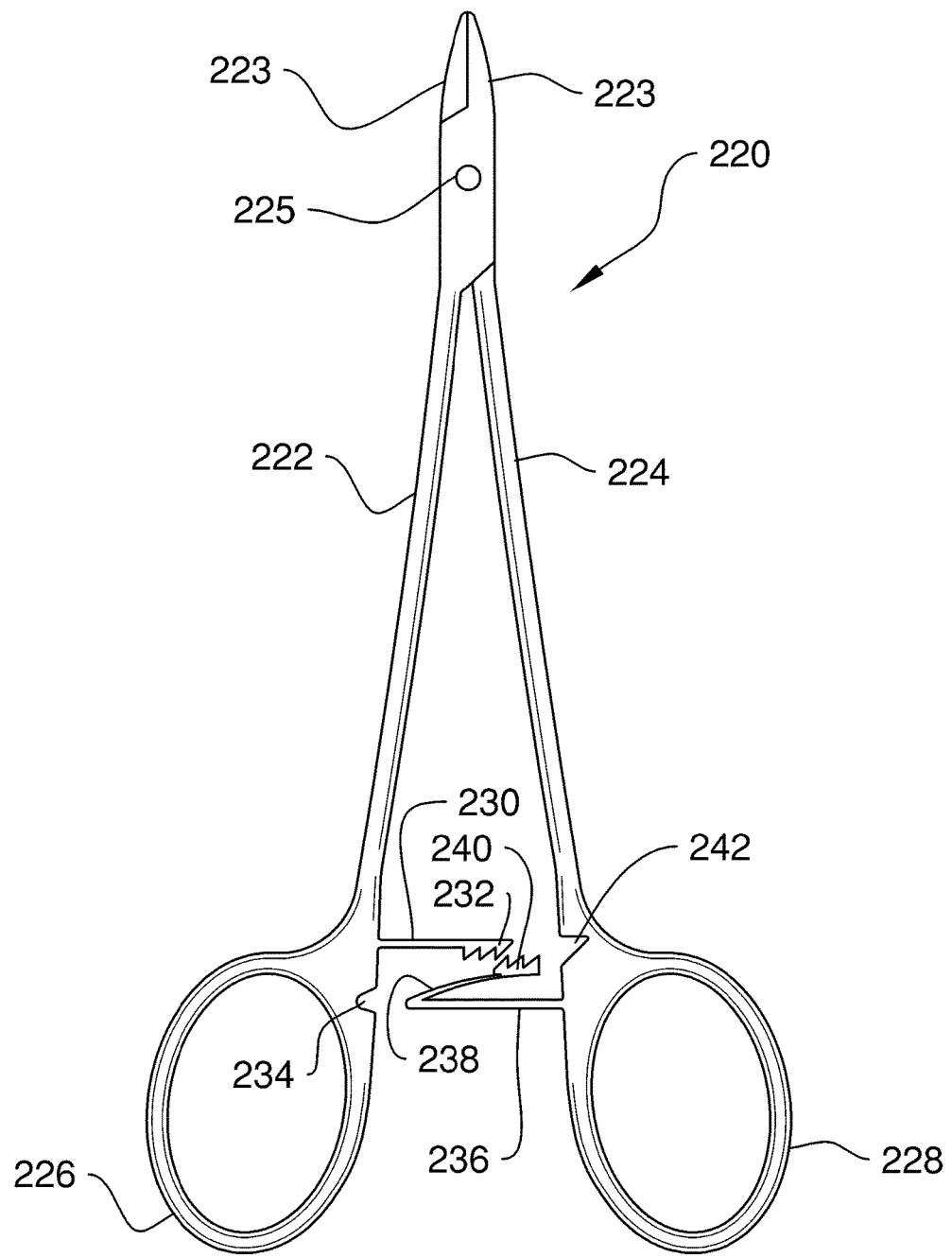
FIG. 20 is a front elevational view of a seventh alternate embodiment of the present invention.

Referring now to FIG. 20, a seventh alternate embodiment of the ambidextrous locking clamp system of the present invention is shown and generally designated by the reference numeral 220. More particularly, the ambidextrous locking clamp system 220 has a first elongated member 222 and a second elongated member 224 each having a working head 223, wherein the working heads can be, but not limited to, a gripping jaw or a cutting edge. The second elongated member 224 is connected to the first elongate member 222 via a hinge 225. The first and second elongated members 222, 224 each have a corresponding finger engaging member 226, 228 located opposite of their respective working heads 223. The first finger engaging member 226 has a latching member 230 extending out therefrom, a ratcheting head 232 located at the free end of the latching member 230, and a notch 234. The ratcheting head 232 features ratcheting teeth thereon. The second finger engaging member 228 has a latching member 236 extending out therefrom, a flexible arm 238, a ratcheting head 240, and a notch 242. The ratcheting head 240 features ratcheting teeth thereon adapted to engage with the ratcheting teeth of the ratcheting head 232 when the first and second finger engaging members 226, 228 are squeezed together.

Figure 21:
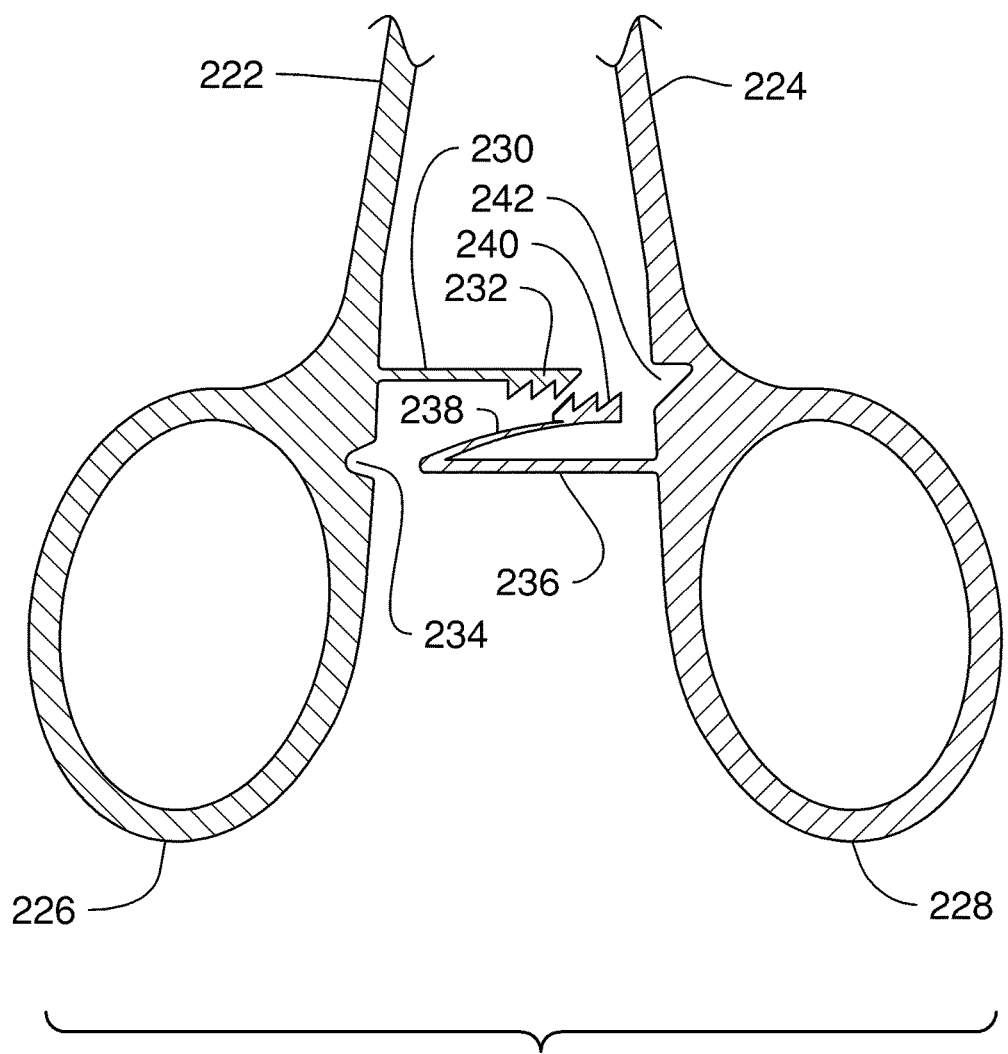
FIG. 21 is an enlarged cross-sectional view of the seventh alternate embodiment of the present invention of FIG. 20.

As illustrated in FIG. 21, the latching member 230 of the first finger engaging member 226 extends out from the first finger engaging member toward the second finger engaging member 228. The notch 234 can have any geometric shape, but preferably a U-shape aligned with the latching member 236. The latching member 230 is positioned above or below the notch 234. The notch 234 is configured to receive the flexible arm 238 and the latching member 236 attachment point. The flexible arm 238 is attached to the free end of the latching member 236, and the ratcheting head 240 is attached to the free end of the flexible arm 238. The latching member 236 of the second finger engaging member 228 extends out from the second finger engaging member 228 toward the notch 234 of the first finger engaging member 226. The flexible arm 238 extends inwardly and upwardly from the free end of the latching member 236, and has an arcuate shape. The flexible arm 238 allows for the free travel of the ratcheting head 240. The notch 242 is positioned above or below the latching member 236 and is aligned with the latching member 230, and is adapted and configured to receive the ratcheting head 232 of the latching member 230. The notch 242 can have any geometric shape, but preferably a shape that corresponds to the shape of the ratcheting head 232 of the latching member 230.

The ratcheting teeth of the ratcheting head 232 and the ratcheting teeth of the ratcheting head 240 are adapted to join and lock together when engaged by squeezing the finger engaging members 226, 228 together. The teeth are able to disengage when pulled apart by flexing the first and second elongated members 222, 224 when an opposing force is applied to the finger engaging members 226, 228 by pushing with the thumb and pulling with the fingers of the operating hand thereby separating the parallel engaged teeth.

It can be appreciated that the ambidextrous locking clamp system 220 can be used with either the left or right hand with identical methods of separating and disengaging the teeth of ratcheting heads 232, 240.

Figure 22:
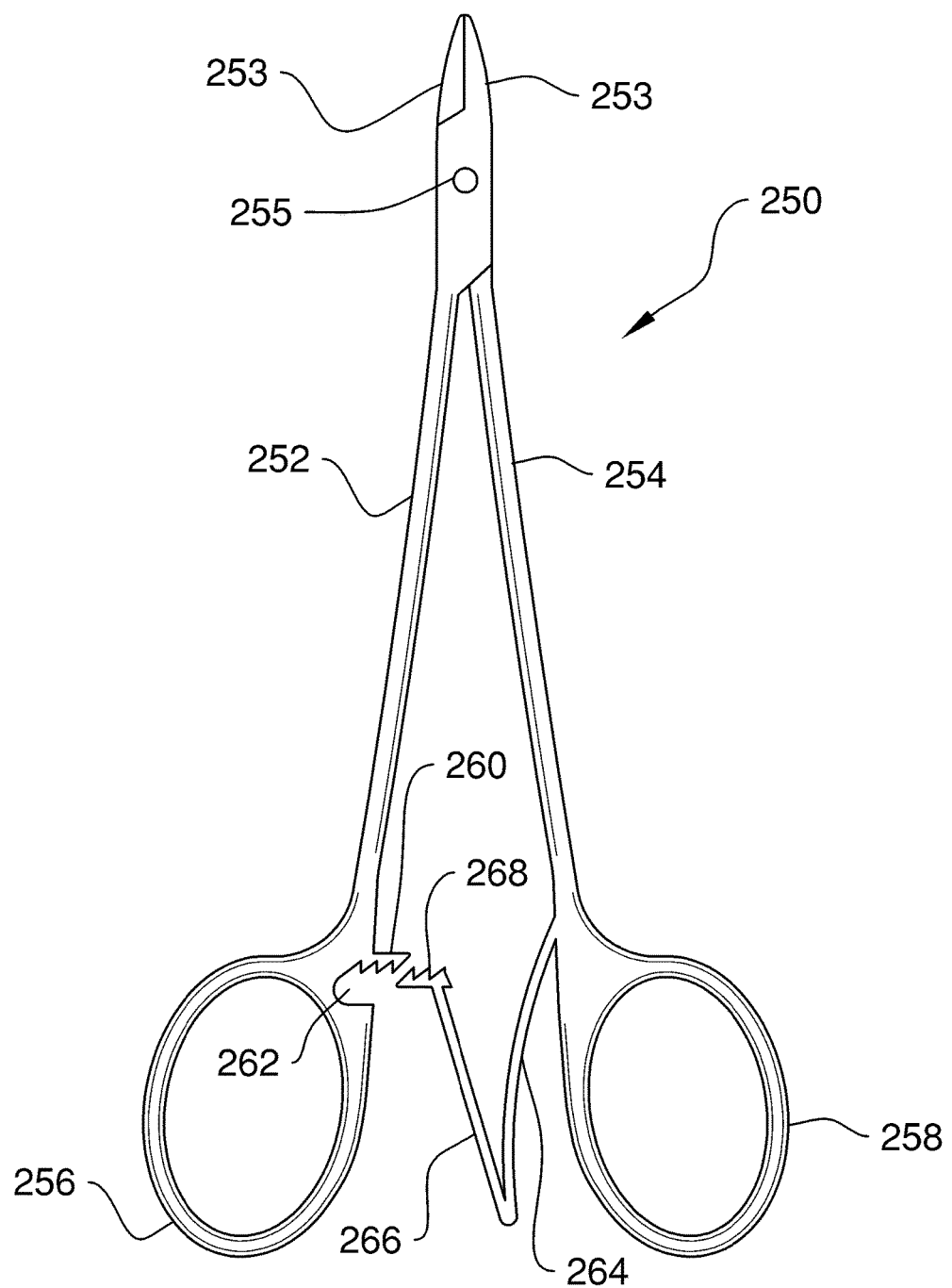
FIG. 22 is a front elevational view of an eighth alternate embodiment of the present invention.

Referring now to FIG. 22, an eighth alternate embodiment of the ambidextrous locking clamp system of the present invention is shown and generally designated by the reference numeral 250. More particularly, the ambidextrous locking clamp system 250 has a first elongated member 252 and a second elongated member 254 each having a working head 253, wherein the working heads can be, but not limited to, a gripping jaw or a cutting edge. The second elongated member 254 is connected to the first elongate member 252 via a hinge 255. The first and second elongated members 252, 254 each have a corresponding finger engaging member 256, 258 located opposite of their respective working heads 253. The first finger engaging member 256 has a latching member 260 extending out therefrom, and a notch 262 adjacent the latching member 260. The latching member 260 features ratcheting teeth thereon. The second finger engaging member 258 has a latching member 264 extending out therefrom, an arm 266, and a ratcheting head 268. The ratcheting head 268 features ratcheting teeth thereon adapted to engage with the ratcheting teeth of the latching member 260 when the first and second finger engaging members 256, 258 are squeezed together.

Figure 23:
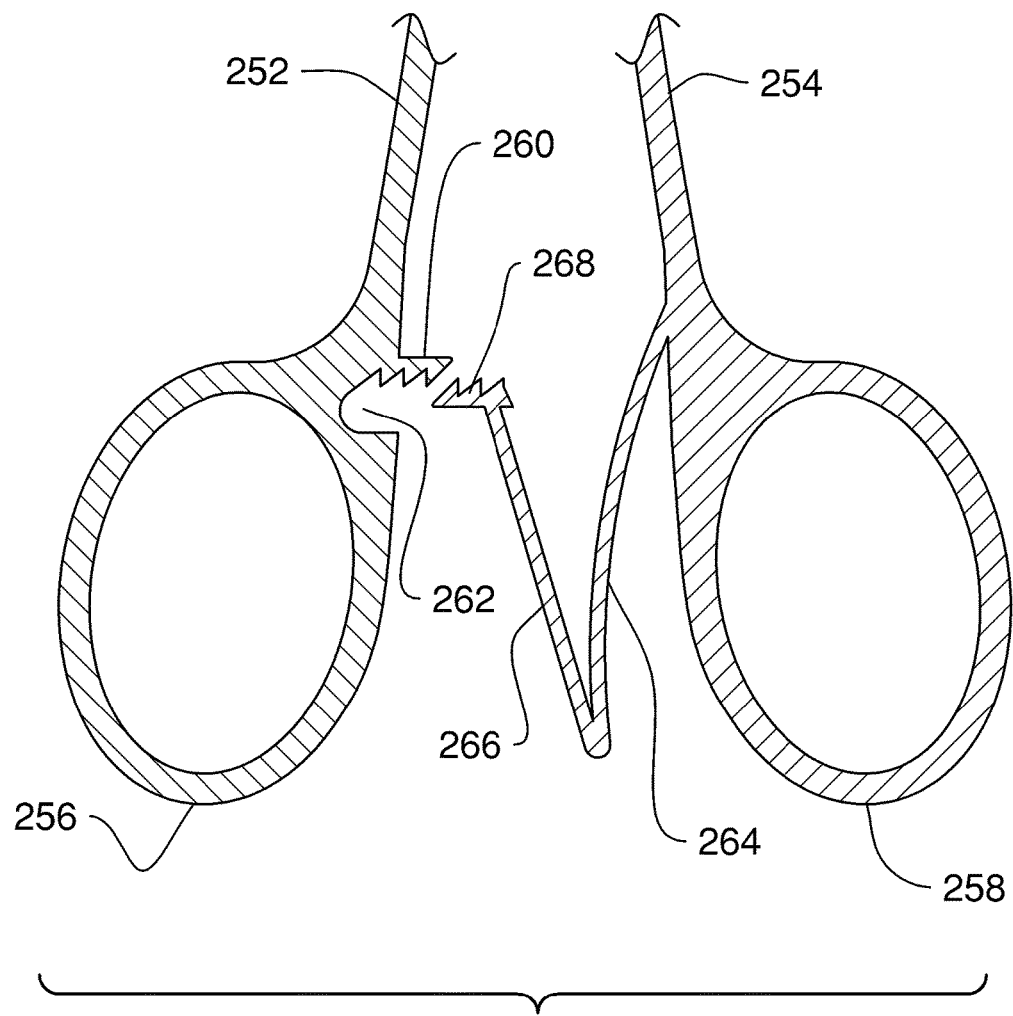
FIG. 23 is an enlarged cross-sectional view of the eighth alternate embodiment of the present invention of FIG. 22.

As illustrated in FIG. 23, the latching member 260 of the first finger engaging member 256 extends out from the first finger engaging member toward the second finger engaging member 258. The notch 262 can have any geometric shape, but preferably a U-shape with the latching member 260 being positioned directly above or below and adjacent to the U-shaped notch. The notch 262 is aligned with the ratcheting head 268 of the latching member 264, allowing the ratcheting head 268 to disengage from the ratcheting head 260, while received therein. The latching member 264 of the second finger engaging member 258 extends out from the second finger engaging member toward the first finger engaging member 256. The arm 266 is attached to the free end of the latching member 264, and the ratcheting head 268 is attached to the free end of the arm 266. The latching member 264 and the arm 266 are flexible allowing for the free travel of the ratcheting head 268, with respect to the second finger engaging member 258. The latching member 264 extends outwardly and downwardly from the interior of the second finger engaging member 258, and has a generally arcuate shape. The arm 266 extends outwardly and upwardly from the free end of the latching member 264.

The ratcheting teeth of the latching member 260 and the ratcheting teeth of the ratcheting head 268 are adapted to join and lock together when engaged by squeezing the finger engaging members 256, 258 together. The teeth are able to disengage when pulled apart by flexing the first and second elongated members 252, 254 when an opposing force is applied to the finger engaging members 256, 258 by pushing with the thumb and pulling with the fingers of the operating hand thereby separating the parallel engaged teeth.

It can be appreciated that the ambidextrous locking clamp system 250 can be used with either the left or right hand with identical methods of separating and disengaging the teeth of the first latching member 260 and the ratcheting head 268.

Figure 24:
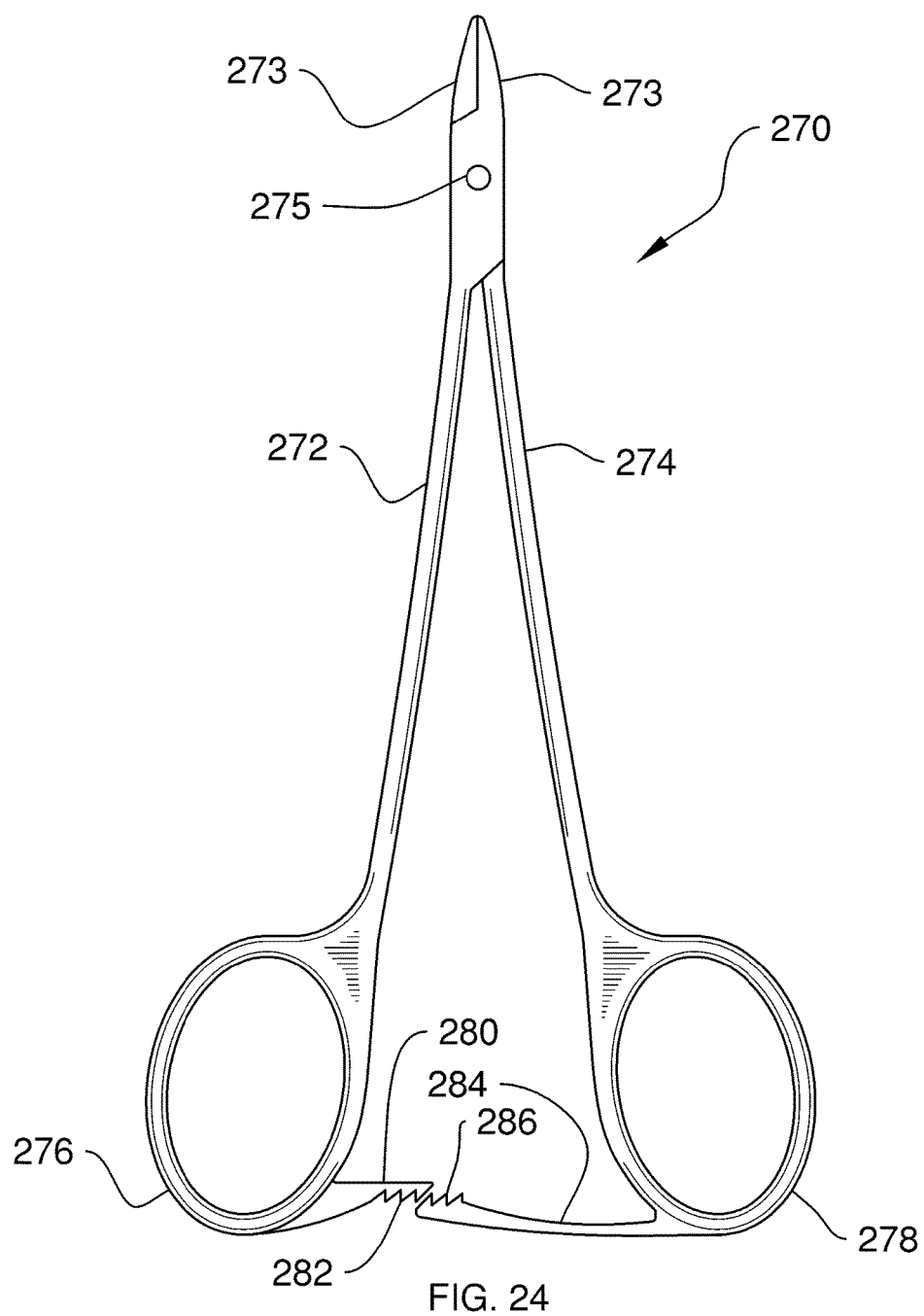
FIG. 24 is a front elevational view of a ninth alternate embodiment of the present invention.

Referring now to FIG. 24, a ninth alternate embodiment of the ambidextrous locking clamp system of the present invention is shown and generally designated by the reference numeral 270. More particularly, the ambidextrous locking clamp system 270 has a first elongated member 272 and a second elongated member 274 each having a working head 273, wherein the working heads can be, but not limited to, a gripping jaw or a cutting edge. The second elongated member 274 is connected to the first elongate member 272 via a hinge 275. The first and second elongated members 272, 274 each have a corresponding finger engaging member 276, 278 located opposite of their respective working heads 273. The first finger engaging member 272 has a latching member 280 extending out therefrom, and a ratcheting head 282. The ratcheting head 282 features ratcheting teeth thereon. The second finger engaging member 278 has a latching member 284 extending out therefrom, and a ratcheting head 286. The ratcheting head 286 features ratcheting teeth thereon adapted to engage with the ratcheting teeth of the ratcheting head 282 when the first and second finger engaging members 276, 278 are squeezed together.

Figure 25:
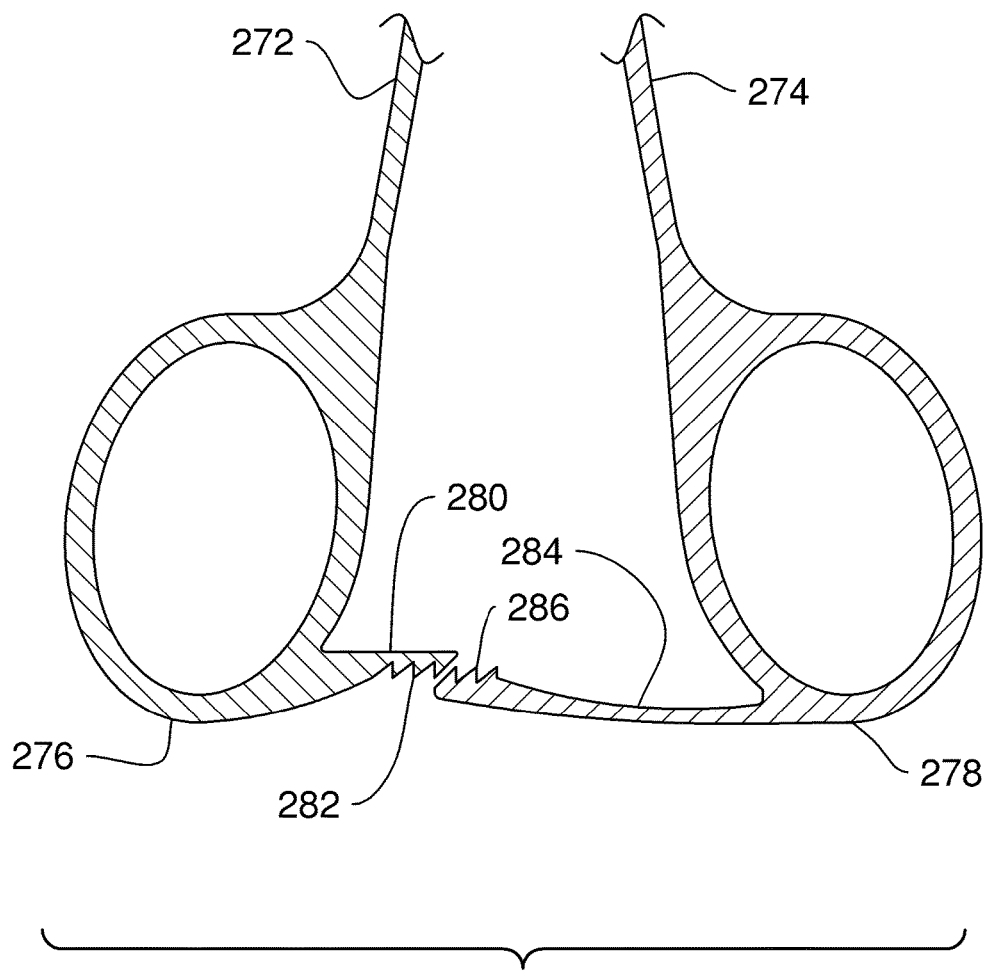
FIG. 25 is an enlarged cross-sectional view of the ninth alternate embodiment of the present invention of FIG. 25.

As illustrated in FIG. 25, the latching member 280 of the first finger engaging member 276 extends out from the bottom of the first finger engaging member toward the second finger engaging member 278. The latching member 284 of the second finger engaging member 278 extends out from the bottom of the second finger engaging member toward the first finger engaging member 276. The bottom side of the latching member 280 has a generally arcuate shape featuring an upwardly curve so as not to interfere with the movement of ratcheting head 286 of the latching member 284 when engaging or disengaging from ratcheting head 282. The latching member 280 is thicker at its attachment point to the first finger engaging member 276 than at its attachment point to the ratcheting head 282. The latching member 284 is a flexible arm, and the ratcheting head 286 is attached to the free end of the flexible arm latching member 284. The flexible arm latching member 284 allows for the free travel of the ratcheting head 286, with respect to the second finger engaging member 278.

The ratcheting teeth of the ratcheting head 282 of latching member 280 and the ratcheting teeth of the ratcheting head 286 are adapted to join and lock together when engaged by squeezing the finger engaging members 276, 278 together. The teeth are able to disengage when pulled apart by flexing the first and second elongated members 272, 274 when an opposing force is applied to the finger engaging members 276, 278 by pushing with the thumb and pulling with the fingers of the operating hand thereby separating the parallel engaged teeth.

It can be appreciated that the ambidextrous locking clamp system 270 can be used with either the left or right hand with identical methods of separating and disengaging the teeth of ratcheting heads 282, 286.

Figure 26:
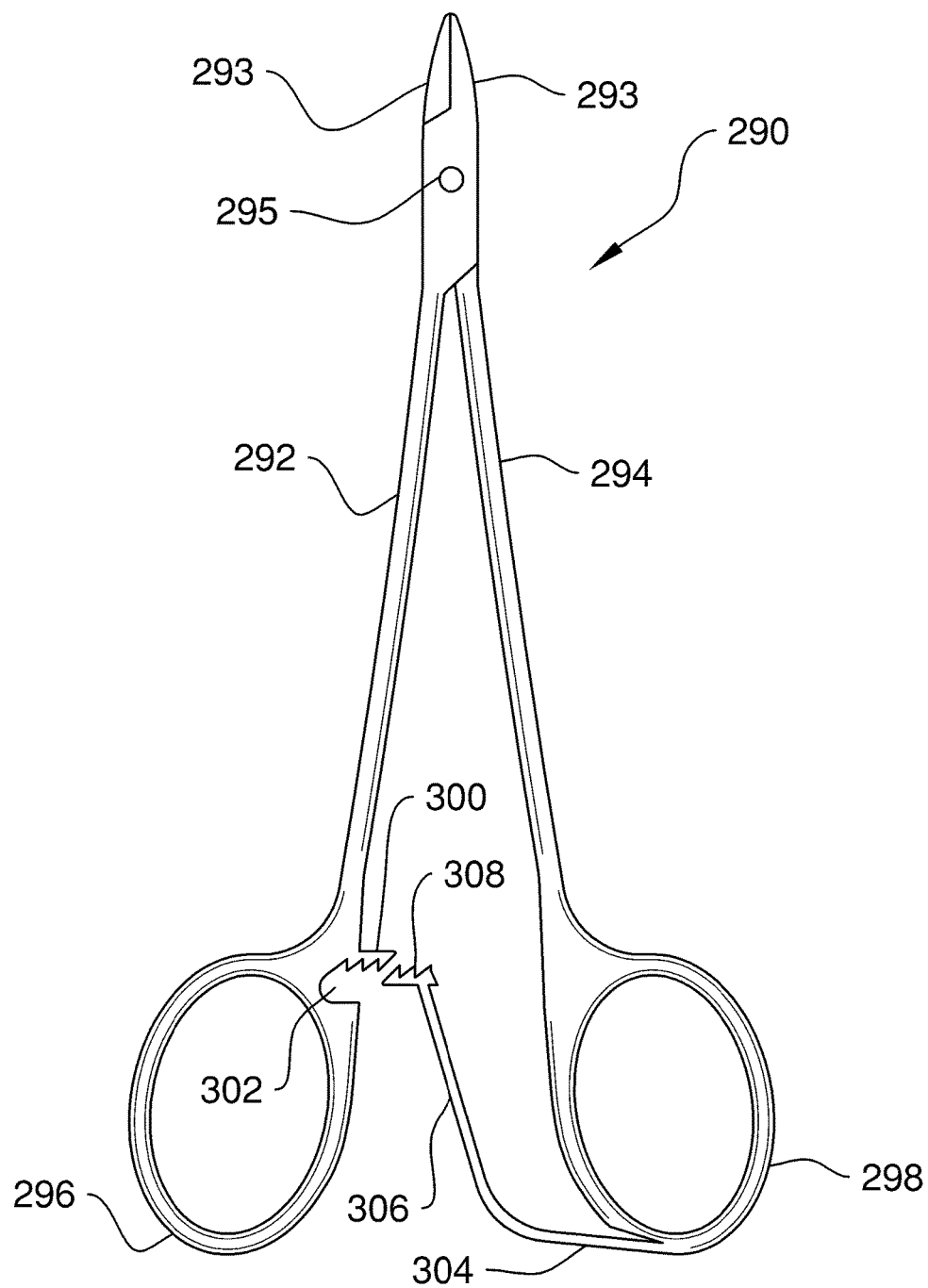
FIG. 26 is a front elevational view of a tenth alternate embodiment of the present invention.

Referring now to FIG. 26, a tenth alternate embodiment of the ambidextrous locking clamp system of the present invention is shown and generally designated by the reference numeral 290. More particularly, the ambidextrous locking clamp system 290 has a first elongated member 292 and a second elongated member 294 each having a working head 293, wherein the working heads can be, but not limited to, a gripping jaw or a cutting edge. The second elongated member 294 is connected to the first elongate member 292 via a hinge 295. The first and second elongated members 292, 294 each have a corresponding finger engaging member 296, 298 located opposite of their respective working heads 293. The first finger engaging member 296 has a latching member 300 extending out therefrom, and a notch 302 adjacent the latching member 300. The latching member 300 features ratcheting teeth thereon. The second finger engaging member 298 has a latching member 304 extending out therefrom, an arm 306, and a ratcheting head 308. The ratcheting head 308 features ratcheting teeth thereon adapted to engage with the ratcheting teeth of the latching member 300 when the first and second finger engaging members 296, 298 are squeezed together.

Figure 27:
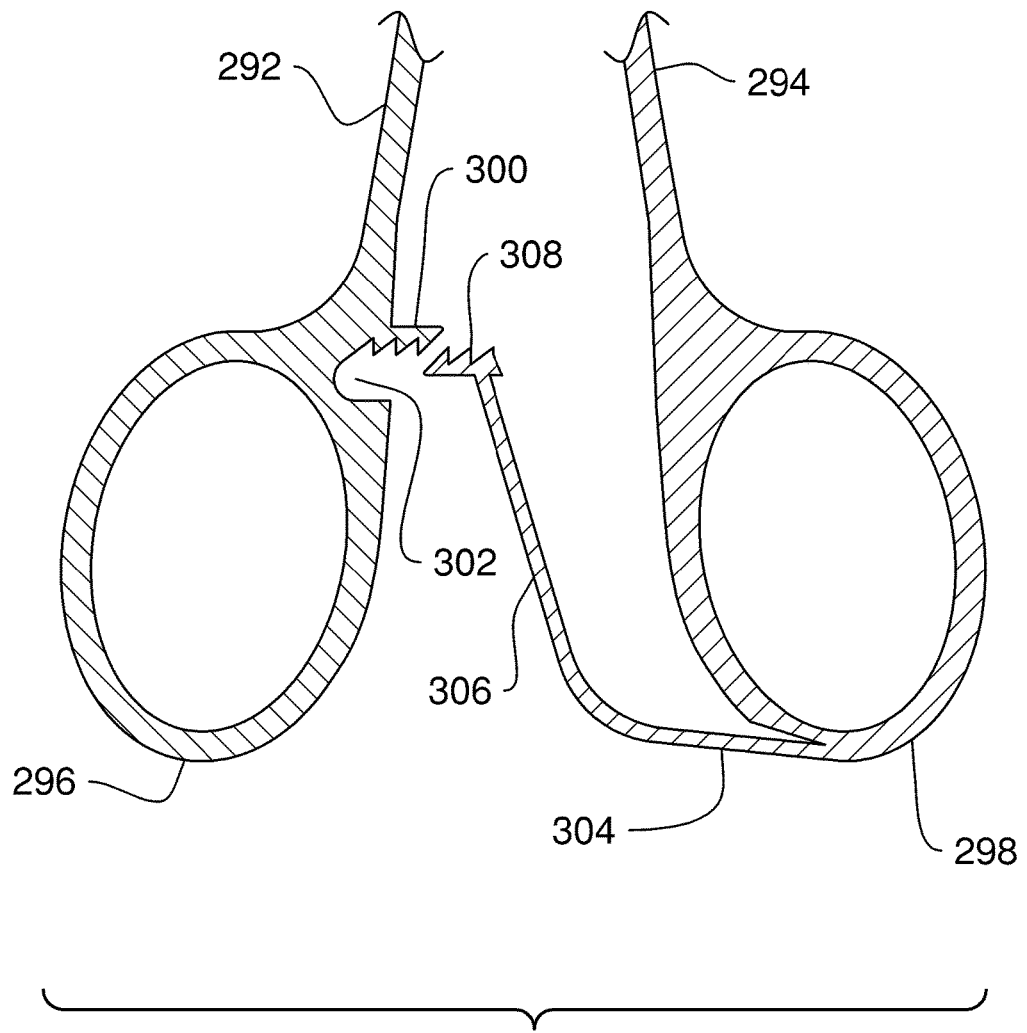
FIG. 27 is an enlarged cross-sectional view of the tenth alternate embodiment of the present invention of FIG. 26.

As illustrated in FIG. 27, the latching member 300 of the first finger engaging member 296 extends out from the first finger engaging member toward the second finger engaging member 298. The notch 302 can have any geometric shape, but preferably a U-shape with the latching member 300 being positioned directly above or below and adjacent to the U-shaped notch. The notch 302 is located so as to be aligned with the ratcheting head 308 of the latching member 304. The notch 302 is configured to receive the ratcheting head 308 of the latching member 304, and to allow the ratcheting head 308 to engage and disengage from latching member 300. The latching member 304 of the second finger engaging member 298 extends out from the bottom of the second finger engaging member toward the first finger engaging member 296. The arm 306 is attached to the free end of the latching member 304 with an arcuate connection, and the ratcheting head 308 is attached to the free end of the arm 306. The latching member 304 and the arm 306 are flexible allowing for the free travel of the ratcheting head 308, with respect to the second finger engaging member 298. The latching member 304 extends outwardly and upwardly from the interior of the second finger engaging member 298, while the arm 306 extends outwardly and upwardly from the free end of the latching member 306.

The ratcheting teeth of the latching member 300 and the ratcheting teeth of the ratcheting head 308 are adapted to join and lock together when engaged by squeezing the finger engaging members 296, 298 together. The teeth are able to disengage when pulled apart by flexing the first and second elongated members 292, 294 when an opposing force is applied to the finger engaging members 296, 298 by pushing with the thumb and pulling with the fingers of the operating hand thereby separating the parallel engaged teeth.

It can be appreciated that the ambidextrous locking clamp system 290 can be used with either the left or right hand with identical methods of separating and disengaging the teeth of the first latching member 300 and the ratcheting head 308.

The latching members 80, 90, 130, 140, 160, 170, 190, 194, 210, 214, 230, 236, 260, 264, 280, 284, 300, 304 can have indicators thereon and can be adapted to be universally used in many orientations.

Figure 28:
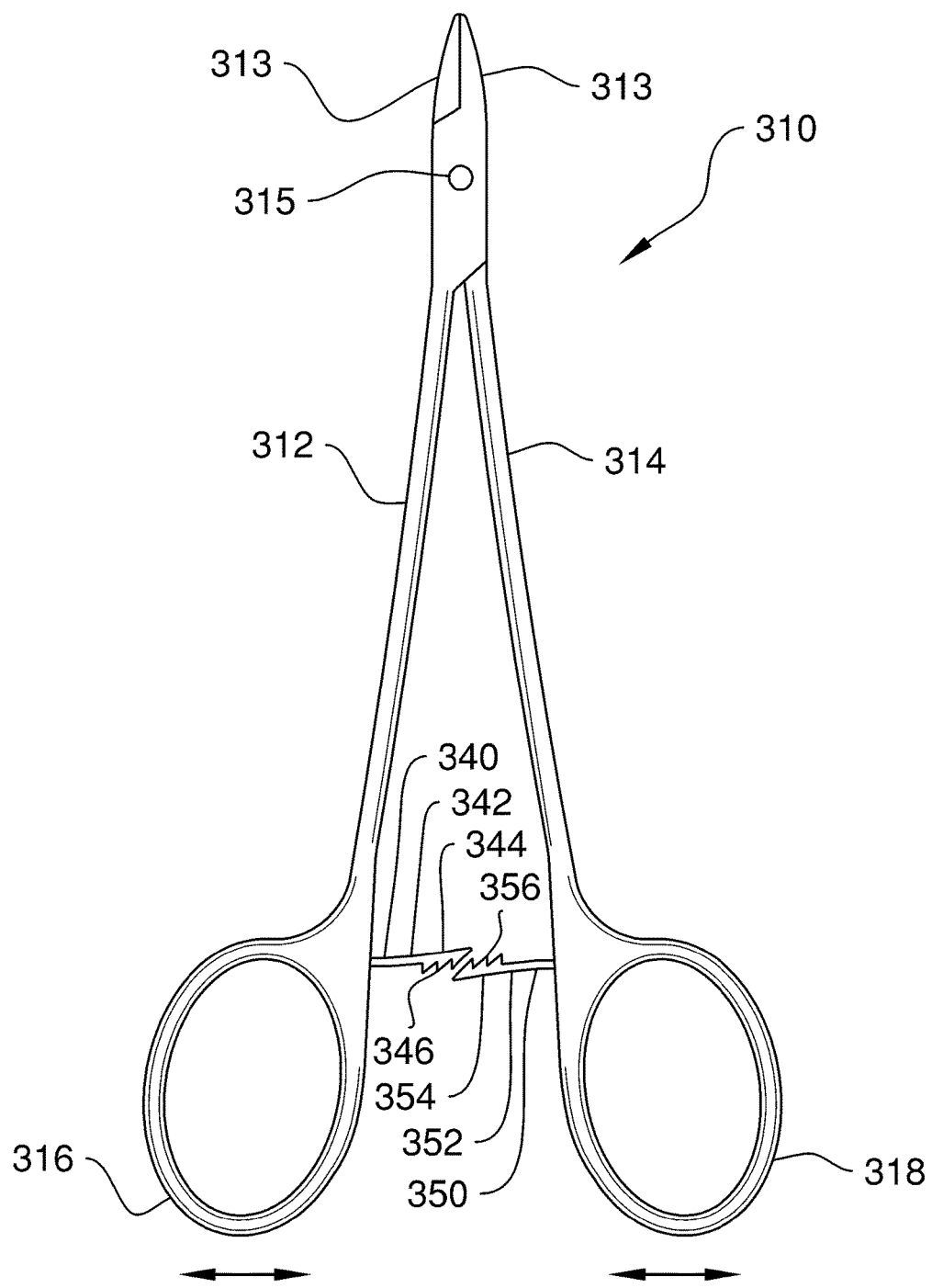
FIG. 28 is a front plane view of the ambidextrous locking clamp system constructed in accordance with the principles of the present invention.

In FIG. 28, a new and improved ambidextrous locking clamp system 310 of the present invention for allowing the use of a hand operated device by a right or left handed user is illustrated and will be described. More particularly, the ambidextrous locking clamp system 310 has a first elongated member 312 and a second elongated member 314 each having a working head 313, wherein the working heads can be, but not limited to, a gripping jaw or a cutting edge. The second elongated member 314 is connected to the first elongated member 312 via a hinge 315. The first elongated member 312 has a first finger engaging member 316 located opposite the working head 313 with the hinge 315 located between the working head 313 and the first finger engaging member 316, and a first latching member 340 extending away from the first elongate member 312 or the first finger engaging member 316. The second elongated member 314 has a second finger engaging member 318 located opposite the working head 313 with the hinge 315 located between the working head 313 and the second finger engaging member 318, and a second latching member 350 extending away from the second elongate member 314 or the second finger engaging member 318. The first and second latching members 340, 350 are oriented toward each other so as to releasably engage with each other. The first and second elongated members 312, 314 can be made from any suitable material having reflex memory.

Figure 29:
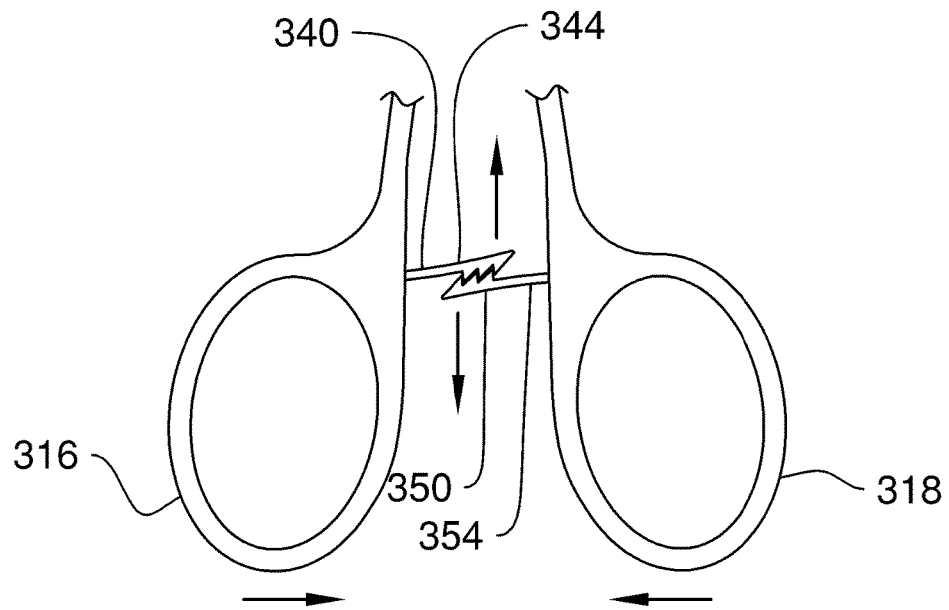
FIG. 29 is an enlarged front plane view of the ratcheting teeth in an engaging configuration of the present invention.

The first and second latching members 340, 350 each have a flexible arm 342, 352, a ratcheting head 344, 354 located at a free end of the flexible arm 342, 352 respectively. The first ratcheting head 344 has a plurality of ratcheting teeth 346 oriented toward or away from the working head 313. The second ratcheting head 354 has a plurality of ratcheting teeth 356 oriented in a direction opposite the first ratcheting head 344 so as to join and lock together when engaged by squeezing the finger engaging members 316, 318 together, as best illustrated in FIG. 29.

It can be appreciated that to operate the working heads 313 a right or left handed user would insert a thumb in either the first or second finger engaging member 316, 318, and at least one finger in the free finger engaging member opposite the one receiving the thumb. The user would then provide an engaging motion until the ratcheting teeth 346, 356 overlap one another in succession until desire tension or working head force is achieved. The engaging motion is produced by moving the finger engaging members 316, 318 of the first and second members 312, 314 toward each other so as to flex the flexible arms 342, 352 away from each other, thereby interlocking the ratcheting teeth 346, 356 together and locking the ambidextrous locking clamp system 310.

Figure 30:
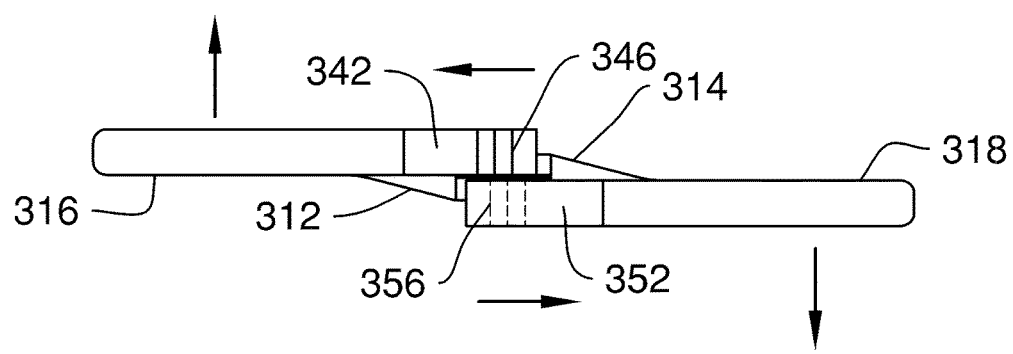
FIG. 30 is an enlarged bottom elevational view of the ratcheting teeth in a disengaging configuration of the present invention.

As best illustrated in FIG. 30, to disengage the ratcheting teeth 346, 356 and release tension or working head force, the user would produce a disengaging motion that is perpendicular to the engaging motion until the ratcheting teeth are slidably disengaged from each other. The disengaging motion is produced by flexing the first and second elongated members 312, 314 in opposite directions by applying an opposing force to the first and second finger engaging members 316, 318 by pushing with the thumb of the operating hand of the user on one of the finger engaging members and pulling with the inserted finger on the other finger engaging member thereby slidably separating the ratcheting teeth. The first and second finger engaging members 316, 318 can then be pulled apart to unlock the ambidextrous locking clamp system 310 or re-engage the ratcheting teeth in a different position so as to change the tension.

Figure 31:
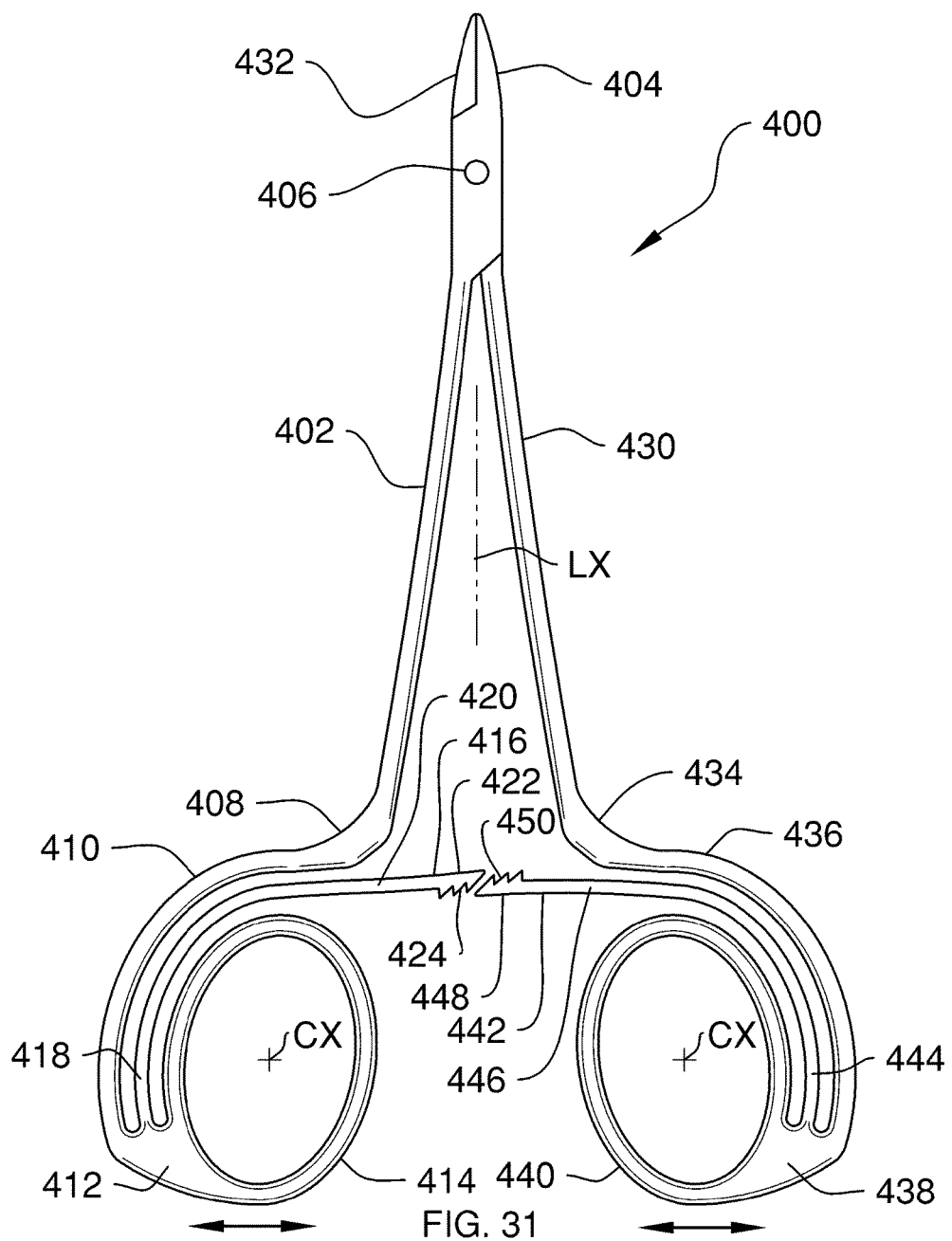
FIG. 31 is a front elevational view of an eleventh alternate embodiment of the present invention.

In FIG. 31, a new and improved ambidextrous locking clamp system 400 of the present invention for allowing the use of a hand operated device by a right or left handed user is illustrated and will be described. More particularly, the ambidextrous locking clamp system 400 has a first elongated member 402 and a second elongated member 430 each having a working head 404, 432, respectively, wherein the working heads can be, but not limited to, a gripping jaw or a cutting edge. The second elongated member 430 is connected to the first elongated member 402 via a hinge 406. The first and second elongated members 402, 430 each have a corresponding finger engaging member 414, 440 located opposite of their respective working heads 404, 432. When assembled, the ambidextrous locking clamp system 400 defines a longitudinal axis LX that passes through the hinge 406.

The first elongated member 402 includes a first finger engaging member arm 410, a first finger engaging member 414, and a first latching member 416. The first finger engaging member arm 410 transitions from an end of the first elongated member 402 by way of a first member transitioning section 408. The first member transitioning section 408 is thicker than the first elongated member 402 and first finger engaging member arm 410. The first member transitioning section 408 extends away from the longitudinal axis LX so as to be exterior of the first elongated member 402.

The first finger engaging member arm 410 has an arcuate or curved profile that extends from the first member transitioning section 408 in a direction away from the longitudinal axis LX so as to be exterior of the first member transitioning section 408 and opposite the working head 404.

The first finger engaging member 414 is located opposite the working head 404 with the hinge 406 located between the working head 404 and the first finger engaging member 414. The first finger engaging member 414 transitions from an end of the first finger engaging member arm 410 by way of a first member finger transitioning section 412. The first member finger transitioning section 412 is thicker than the first finger engaging member arm 410 and the first finger engaging member 414. The first member finger transitioning section 412 extends toward the longitudinal axis LX so as to be interior of the first finger engaging member arm 410. Consequently, the first finger engaging member 414 is interior of the first finger engaging member arm 410 toward the longitudinal axis LX.

The first finger engaging member 414 defines a substantially circular or oval opening having a central axis CX and a configuration capable of receiving at least one finger or digit of a user. The first finger engaging member 414 has a portion thereof in a spaced or offset relationship from the first finger engaging member arm 410 so as to define a space therebetween. The portion of the first finger engaging member 414 that is offset from the first finger engaging member arm 410 has an arcuate or curved profile that corresponds with that of the first finger engaging member arm 410.

Figure 32:
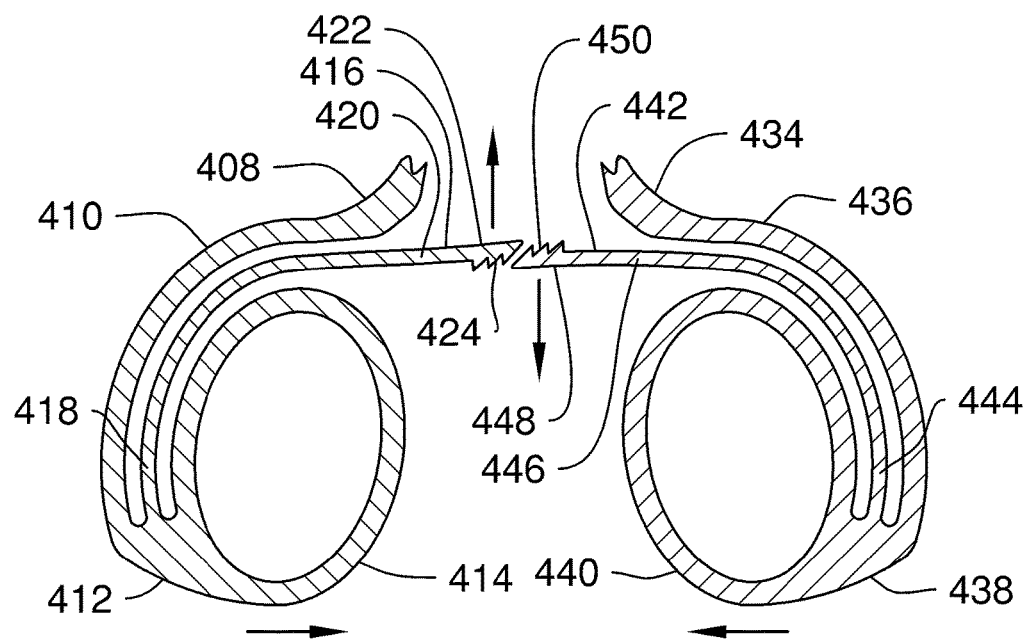
FIG. 32 is an enlarged cross-sectional view of the eleventh alternate embodiment of the present invention of FIG. 31.

As illustrated in FIG. 32, the first latching member 416 has a first arm section 418, a second arm section 420, and a ratcheting head 422. The first arm section 418 extends away from the first member finger transitioning section 412 in the space between the first finger engaging member arm 410 and the first finger engaging member 414. The first arm section 418 has an arcuate or curved profile that corresponds with that of the first finger engaging member arm 410 and the portion of the first finger engaging member 414 that is offset from the first finger engaging member arm 410. Consequently, the first arm section 418 defines a gap between the first finger engaging member arm 410 and the portion of the first finger engaging member 414 that is offset from the first finger engaging member arm 410.

The second arm section 420 extends away from the first arm section 418 toward the longitudinal axis LX. The ratcheting head 422 is located at a free end of the second arm section 420. The ratcheting head 422 features ratcheting teeth 424 extending in a direction aligned with the longitudinal axis LX.

The second elongated member 430 is similar in structure to and a mirror of the first elongated member 402. The second elongated member 430 includes a second finger engaging member arm 436, a second finger engaging member 440, and a second latching member 442. The second finger engaging member arm 436 transitions from an end of the second elongated member 430 by way of a second member transitioning section 434. The second member transitioning section 434 is thicker than the second elongated member 430 and the second finger engaging member arm 436. The second member transitioning section 434 extends away from the longitudinal axis LX so as to be exterior of the second elongated member 430.

The second finger engaging member arm 436 has an arcuate or curved profile that extends from the second member transitioning section 434 in a direction away from the longitudinal axis LX so as to be exterior of the second member transitioning section 434 and opposite the working head 432.

The second finger engaging member 440 is located opposite the working head 432 with the hinge 406 located between the working head 432 and the second finger engaging member 440. The second finger engaging member 440 transitions from an end of the second finger engaging member arm 436 by way of a second member finger transitioning section 438. The second member finger transitioning section 438 is thicker than the second finger engaging member arm 436 and the second finger engaging member 440. The second member finger transitioning section 438 extends toward the longitudinal axis LX so as to be interior of the second finger engaging member arm 436. Consequently, the second finger engaging member 440 is interior of the second finger engaging member arm 436 toward the longitudinal axis LX.

The second finger engaging member 440 defines a substantially circular or oval opening having a central axis CX and a configuration capable of receiving at least one finger or digit of the user. The second finger engaging member 440 has a portion thereof in a spaced or offset relationship from the second finger engaging member arm 436 so as to define a space therebetween. The portion of the second finger engaging member 440 that is offset from the second finger engaging member arm 436 has an arcuate or curved profile that corresponds with that of the second finger engaging member arm 436.

As illustrated in FIG. 32, the second latching member 442 has a first arm section 444, a second arm section 446, and a ratcheting head 448. The first arm section 444 extends away from the second member finger transitioning section 438 in the space between the second finger engaging member arm 436 and the second finger engaging member 440. The first arm section 444 has an arcuate or curved profile that corresponds with that of the second finger engaging member arm 436 and the portion of the second finger engaging member 440 that is offset from the second finger engaging member arm 436. Consequently, the first arm section 444 defines a gap between the second finger engaging member arm 436 and the portion of the second finger engaging member 440 that is offset from the second finger engaging member arm 436.

The second arm section 446 extends away from the first arm section 444 toward the longitudinal axis LX. The ratcheting head 448 is located at a free end of the second arm section 446. The ratcheting head 448 features ratcheting teeth 450 extending in a direction aligned with the longitudinal axis LX.

The first and second elongated members 402, 430, the first and second finger engaging member arms 410, 436, the first arm sections 418, 444 of the first and second latching members 416, 442 and/or the second arm sections 420, 446 of the first and second latching members 416, 442 can be made from any suitable material having reflex memory.

Figure 33:
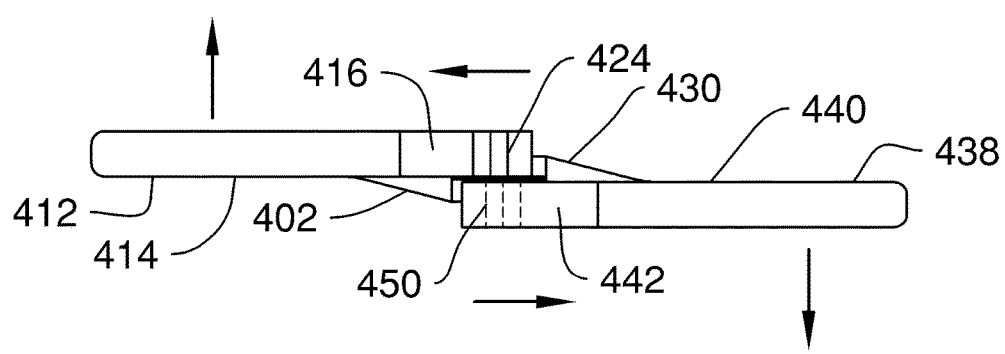
FIG. 33 is an enlarged bottom elevational view of the ratcheting teeth in a disengaging configuration of the embodiment of the present invention of FIG. 31.

As illustrated in FIG. 33, the ratcheting teeth 424, 450 of the first and second latching members 416, 442 are adapted to join and lock together when engaged by squeezing the first and second finger engaging members 414, 440 together. It can be appreciated that to operate the working heads 404, 432 a right or left handed user would insert a thumb in either the first or second finger engaging member 414, 440, and insert at least one finger in the free finger engaging member opposite the one receiving the thumb. The user would then provide an engaging motion until the ratcheting teeth 424, 450 overlap one another in succession until desire tension or working head force is achieved. The engaging motion is produced by moving the first and second finger engaging members 414, 440 of the first and second elongated members 402, 430 toward each other so that the ratcheting heads 422, 448 move toward each other, thereby interlocking the ratcheting teeth 424, 450 together and locking the ambidextrous locking clamp system 400.

The ratcheting heads 422, 448, respectively, can move by:

Pivoting the first and second finger engaging members 414, 440 about the first and second member transitioning sections 408, 434;

Flexing the first and second finger engaging member arms 410, 436;

Pivoting the first arm sections 418, 444 about the first and second member finger transitioning sections 412, 438;

Flexing the first arm sections 418, 444; and/or

Flexing the second arm sections 420, 446.

To disengage the ratcheting teeth 424, 450 and release tension of working head force, the user would produce a disengaging motion that is perpendicular to the engaging motion until the ratcheting teeth 424, 450 are slidably disengaged from each other. The disengaging motion may be produced by moving the first and second elongated members 402, 430 in opposite directions by applying an opposing force to the first and second finger engaging members 414, 440 by pushing with the thumb of the operating hand of the user on one of the finger engaging members and pulling with the inserted finger on the other finger engaging member thereby slidably separating the ratcheting teeth. The first and second finger engaging members 414, 440 can then be pulled apart to unlock the ambidextrous locking clamp system 400 or re-engage the ratcheting teeth in a different position so as to change the tension.

It can be appreciated that the engaging and disengaging motions can be initiated by either a left or right handed user in the same manner by simply inserting the thumb of the operating hand in one of the first and second finger engaging members 414, 440 and the at least one finger of the same operating hand in the other finger engaging member.

The latching members 416, 442 can have indicators thereon and can be adapted to be universally used in many orientations.

The above described engaging and disengaging motion can be used for all embodiments of the present invention, and in use, it can now be understood that either a right hand or left hand user can operate the ambidextrous locking clamp system. As described above, the user would apply opposing force to the finger engaging members pushing with the thumb and pulling with the fingers of the operating hand thereby separating the engaged teeth of the first and second latching members.

While a preferred embodiment of the ambidextrous locking clamp system has been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. For example, any suitable sturdy material may be used for the manufacture of the ambidextrous locking clamp system, such as but not limited to, steel, aluminum, plastics, and composites. And although manipulating objects with a tool having latching members have been described, it should be appreciated that the ambidextrous locking clamp system herein described is also suitable for all types of hand operated locking tools having a at least two hingedly connected arms.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An ambidextrous locking clamp for allowing a right hand or left hand user to operate said clamp, said ambidextrous locking clamp comprising:
   at least one first member comprising:
      at least one first elongated body including at least one first working head located at an end of said first elongated body;
      at least one first finger engaging member arm transitioning from said first elongated body;
      at least one first finger engaging member transitioning from said first finger engaging member arm defining a first member space between at least a section of an interior side of said first finger engaging member arm and at least a section of an exterior side of said first finger engaging member, said section of said interior side of said first finger engaging member arm and said section of said exterior side of said first finger engaging member face each other in a side-by-side configuration; and
      at least one first latching member extending through said first member space, said first latching member including at least one first latching member head, said first latching member head including first member ratcheting teeth,
   at least one second member comprising:
      at least one second elongated body including at least one second working head located at an end of said second elongated body;
      at least one second finger engaging member arm transitioning from said second elongated body;
      at least one second finger engaging member transitioning from said second finger engaging member arm defining a second member space between at least a section of an interior side of said second finger engaging member arm and at least a section of an exterior side of said second finger engaging member, said section of said interior side of said second finger engaging member arm and said section of said exterior side of said second finger engaging member face each other in a side-by-side configuration; and
      at least one second latching member extending through said second member space, said second latching member including at least one second latching member head, said second latching member head including second member ratcheting teeth, said second member ratcheting teeth extending toward said first member ratcheting teeth;
   wherein said first and second members being pivotably connected so that said first and second working heads face each other and are moved toward each other when said first and second finger engaging member are moved toward each other;
   wherein said first and second member ratcheting teeth being orientated so as to be engageable with each other by an engaging motion when said first and second finger engaging members are moved toward each other;
   wherein said first and second member ratcheting teeth having a configuration capable of disengaging with each other by sliding said first and second member ratcheting teeth apart by a disengaging motion perpendicular to said engaging motion resulting in moving said first and second latching members away from each other when an opposing force is applied to said first and second finger engaging members.

2. The ambidextrous locking clamp of claim 1, wherein said first and second finger engaging members have a configuration capable of producing said disengaging motion by pushing with a thumb of an operating hand of a user on one of said first and second finger engaging members and pulling with at least one finger of the operating hand on the other of said first and second finger engaging member thereby slidably separating said first and second ratcheting teeth.

3. The ambidextrous locking clamp of claim 1, wherein said first finger engaging member arm extends from said first elongated body away from a longitudinal axis of said ambidextrous locking clamp, said second finger engaging member arm extends from said second elongated body away from said longitudinal axis in a direction opposite said first engaging member arm.

4. The ambidextrous locking clamp of claim 1, wherein said first and second finger engaging members are arranged between said section of said first and second finger engaging member arms.

5. The ambidextrous locking clamp of claim 1, wherein said first latching member extends from a first member transitioning area where said first finger engaging member transitions from said first finger engaging member arm, and said second latching member extends from a second member transitioning area where said second finger engaging member transitions from said second finger engaging member arm.

6. The ambidextrous locking clamp of claim 5, wherein said first and second latching members each featuring a first arm section, and a second arm section extending from said first arm section, respectively, said first arm section of said first latching member extends from said first member transitioning area and is received in said first member space, said first arm section of said second latching member extends from second member transitioning area and is received in said second member space.

7. The ambidextrous locking clamp of claim 6, wherein said first and second finger engaging member arms each have at least a first portion featuring a first arcuate profile, respectively.

8. The ambidextrous locking clamp of claim 7, wherein said first and second finger engaging members each have at least a second portion featuring a second arcuate profile, respectively.

9. The ambidextrous locking clamp of claim 8, wherein said first arcuate profile of said first finger engaging member arm corresponds with said second arcuate profile of said first finger engaging member, said first arcuate profile of said second finger engaging member arm corresponds with said second arcuate profile of said second finger engaging member.

10. The ambidextrous locking clamp of claim 9, wherein said first arm section of said first and second latching members each have a third arcuate profile, respectively.

11. The ambidextrous locking clamp of claim 10, wherein said third arcuate profile of said first arm section of said first latching member corresponds said first arcuate profile of said first finger engaging member arm and said second arcuate profile of said first finger engaging member, said third arcuate profile of said second arm section of said second latching member corresponds said first arcuate profile of said second finger engaging member arm and said second arcuate profile of said second finger engaging member.

12. The ambidextrous locking clamp of claim 6, wherein said first latching member is located between said first working head and from where said first finger engaging member transitions from said first finger engaging member arm, said second latching member is located between said second working head and from where said second finger engaging member transitions from said second finger engaging member arm.

13. The ambidextrous locking clamp of claim 12, wherein said first arm section of said first and second latching members each extend toward said first and second working heads, respectively.

14. The ambidextrous locking clamp of claim 13, wherein said first and second finger engaging members each define an opening featuring a central axis, respectively.

15. The ambidextrous locking clamp of claim 14, wherein said central axis of said first finger engaging member is located between said first latching member head and said first member transitioning area, said central axis of said second finger engaging member is located between said second latching member head and said second member transitioning area.

16. The ambidextrous locking clamp of claim 15, wherein said first elongated body is located between a longitudinal axis of said ambidextrous locking clamp and said central axis of said first finger engaging member, said second elongated body is located between said longitudinal axis and said central axis of said second finger engaging member.

17. A method of using an ambidextrous locking clamp, said method comprising the steps of:
   a) configuring a first finger engaging member of a first member to be operated by at least a thumb or a finger of an operating hand of a user, said first member being pivotable connected with a second member, said first member further including a first elongated body, a first working head, a first finger engaging member arm transitioning from said first elongated body, and a first latching member extending through a first member space defined between at least a section of an interior side of said first finger engaging member arm and at least a section of an exterior side of said first finger engaging member, said first latching member extending through said first member space, said section of said interior side of said first finger engaging member arm and said section of said exterior side of said first finger engaging member face each other in a side-by-side configuration;
   b) configuring a second finger engaging member of a second member to be operated by at least the thumb or the finger of the operating hand of the user, said second member further including a second elongated body, a second working head, a second finger engaging member arm transitioning from said second elongated body, and a second latching member extending through a second member space defined between at least a section of an interior side of second first finger engaging member arm and at least a section of an exterior side of said second finger engaging member, said second latching member extending through said second member space, said section of said interior side of said second finger engaging member arm and said section of said exterior side of said second finger engaging member face each other in a side-by-side configuration;
   c) engaging ratcheting teeth of said first and second latching members with each other by an engaging motion until said ratcheting teeth of said first and second latching members overlap one another in succession to a user desired tension, said engaging motion being produced by moving said first and second finger engaging members toward each other; and
   d) disengaging said ratcheting teeth of said first and second latching members by a disengaging motion perpendicular to said engaging motion until said ratcheting teeth are slidably disengaged, said disengaging motion being produced by moving said first and second members in opposite directions when an opposing force is applied to said first and second finger engaging members by pushing with the thumb of the operating hand on at least one of said first and second finger engaging members and pulling with the finger of the operating hand on the other of said first and second finger engaging members thereby slidably separating said ratcheting teeth of said first and second latching members out of engagement.

18. The ambidextrous locking clamp of claim 1, wherein said section of said first and second finger engaging member arms has a profile matching and receiving a profile of said section of said first and second finger engaging member, respectively.

19. The ambidextrous locking clamp of claim 1, wherein said section of said first and second finger engaging member arms and said section of said first and second finger engaging members, respectively, are concentric.

20. The method of claim 17, wherein said section of said first and second finger engaging member arms and said section of said first and second finger engaging members, respectively, are concentric.

* * * * *